US009917955B2

(12) United States Patent
Derhak et al.

(10) Patent No.: US 9,917,955 B2
(45) Date of Patent: Mar. 13, 2018

(54) SPECTRAL TRANSMISSIVE MEASUREMENT OF MEDIA

(71) Applicant: Onyx Graphics, Inc., Salt Lake City, UT (US)

(72) Inventors: Maxim Wasyl Derhak, Brighton, NY (US); Lin Luo, Draper, UT (US); Douglas Nolan Mackay, Salt Lake City, UT (US); William Irel Chase, Herriman, UT (US); Lin Chen, Chicago, IL (US)

(73) Assignee: Onyx Graphics, Inc., Salt Lake City, UT (US)

( * ) Notice: Subject to any disclaimer, the term of this patent is extended or adjusted under 35 U.S.C. 154(b) by 0 days.

(21) Appl. No.: 15/423,301

(22) Filed: Feb. 2, 2017

(65) Prior Publication Data

US 2017/0223197 A1    Aug. 3, 2017

Related U.S. Application Data

(60) Provisional application No. 62/290,867, filed on Feb. 3, 2016.

(51) Int. Cl.
*G01N 21/59* (2006.01)
*H04N 1/00* (2006.01)
(Continued)

(52) U.S. Cl.
CPC ....... *H04N 1/00087* (2013.01); *G01N 21/274* (2013.01); *G01N 21/59* (2013.01);
(Continued)

(58) Field of Classification Search
CPC combination set(s) only.
See application file for complete search history.

(56) References Cited

U.S. PATENT DOCUMENTS 5,319,437 A    6/1994  Van Aken
6,346,984 B2   2/2002  Baker
(Continued)

OTHER PUBLICATIONS

Gigahertz-Optik, LCRT-2005-S Portable Spectrophotometer for Transmission Measurement, Nov. 2008.
(Continued)

*Primary Examiner* — Barbara Reinier
(74) *Attorney, Agent, or Firm* — Canon U.S.A., Inc. IP Division

(57) ABSTRACT

Systems, devices, and methods illuminate one or more areas on a calibration medium from a first side of the calibration medium with one or more respective light-emitting regions of a light source; detect light transmitted through the calibration medium at the one or more areas, thereby obtaining calibration-measurement information for at least one of the one or more light-emitting regions; illuminate one or more color patches on a color-measurement medium from a first side of the color-measurement medium with the one or more respective light-emitting regions of the light source; detect light transmitted through the one or more color patches printed on the color-measurement medium, thereby obtaining color-measurement information for at least one of the one or more light-emitting regions; and generate one or more transmissive measurements based on the calibration-measurement information and the color-measurement information.

20 Claims, 13 Drawing Sheets

(51) Int. Cl.
*G01N 21/27* (2006.01)
*H04N 1/60* (2006.01)
*G06K 15/02* (2006.01)

(52) U.S. Cl.
CPC ....... *G06K 15/027* (2013.01); *H04N 1/00023* (2013.01); *H04N 1/00034* (2013.01); *H04N 1/00037* (2013.01); *H04N 1/00058* (2013.01); *H04N 1/6097* (2013.01); *G01N 2201/062* (2013.01); *G01N 2201/127* (2013.01); *G06K 2215/0094* (2013.01); *G06K 2215/0097* (2013.01); *H04N 2201/0082* (2013.01)

(56) References Cited

U.S. PATENT DOCUMENTS

| | | |
|---|---|---|
| 7,298,526 B2 | 11/2007 | Bailey |
| 2005/0219364 A1 | 10/2005 | DiCarlo |
| 2007/0097412 A1 | 5/2007 | Peiro |
| 2007/0262235 A1 | 11/2007 | Pertsel |
| 2010/0148083 A1 | 6/2010 | Brown |
| 2012/0250014 A1 | 10/2012 | Hayashi |
| 2014/0111836 A1 | 4/2014 | Aharon |
| 2014/0131578 A1 | 5/2014 | Hruska |
| 2014/0267866 A1 | 9/2014 | Short |
| 2015/0125668 A1* | 5/2015 | Matsumoto ............... B44F 1/02 428/195.1 |

OTHER PUBLICATIONS

Barbieri, Intelligent Measuring Technology when Color Quality counts, Feb. 2015.
Barbieri, How to measure Glass/Plexiglass, Oct. 2009.
X-Rite Color Services, Monitor Profiling With iProfiler, Aug. 2013.
BARBIERIelectronic, BARBIERI Spectro LFP: Measuring-Glass, https://www.youtube.com/watch?v=6VIFVPxzna4, uploaded on Apr. 15, 2010.

* cited by examiner

SPECTRAL TRANSMISSIVE MEASUREMENT OF MEDIA

CROSS-REFERENCE TO RELATED APPLICATIONS

This application claims the benefit of U.S. Provisional Application No. 62/290,867, which was filed on Feb. 3, 2016.

BACKGROUND

Technical Field

This description generally relates to methods, systems, and devices for obtaining spectral transmissive measurements of media, for example to obtain color information that can be used for color management, such as for color-profile creation or color calibration.

Background

Backlit displays have become increasingly popular for displaying images, such as pictures and graphics, in a variety of different settings, for example retail displays, storefront signs, and tradeshow displays. In a typical backlit display, a light panel is used to illuminate a medium that is at least partially translucent or transparent, and on which an image has been printed. The light panel illuminates the medium from the back, such that light from the light panel passes through the image printed on the medium, thereby illuminating the image as seen by a viewer from the front of the medium. The illumination of a printed image using a backlit display can produce rich colors with especially clear dark tones and shadows, which are eye-catching and aesthetically pleasing.

SUMMARY

Color information for printing on media for a backlit display with a printing apparatus is obtained by illuminating a plurality of areas on a calibration medium from a first side of the calibration medium, with a light source having a plurality of light-emitting regions, and detecting light transmitted through the calibration medium at one or more of the plurality of areas. One or more color patches are printed on a color-measurement medium with the printing apparatus, and a plurality of areas are illuminated on the color-measurement medium from a first side of the color-measurement medium, with the light source. Light transmitted through at least one of the one or more color patches printed on the color-measurement medium is detected, to obtain color-measurement information, and color information is determined based on a relationship between the calibration-measurement information and the color-measurement information.

Some embodiments of a method comprise illuminating one or more areas on a calibration medium from a first side of the calibration medium with one or more respective light-emitting regions of a light source; detecting, at a second side of the calibration medium that is opposite to the first side, light transmitted through the calibration medium at the one or more areas, thereby obtaining calibration-measurement information for at least one of the one or more light-emitting regions; illuminating one or more color patches on a color-measurement medium from a first side of the color-measurement medium with the one or more respective light-emitting regions of the light source; detecting, at a second side of the color-measurement medium that is opposite to the first side, light transmitted through the one or more color patches printed on the color-measurement medium, thereby obtaining color-measurement information for at least one of the one or more light-emitting regions; and determining one or more transmissive measurements based on the calibration-measurement information and the color-measurement information.

Some embodiments of a system comprise one or more computer-readable media and one or more processors that are coupled to the one or more computer-readable media. The one or more processors are configured to cause the system to obtain a first calibration radiance measurement from a detector, wherein the first calibration radiance measurement is a measurement of light that is emitted by a first light-emitting region of a light source on a first side of a calibration medium, that is transmitted through the calibration medium at a first area, and that is measured by the detector on a second side of the calibration medium that is opposite to the first side; obtain a first color radiance measurement from the detector, wherein the first color radiance measurement is a measurement of light that is emitted by the first light-emitting region of the light source on a first side of a color-measurement medium, that is transmitted through the color-measurement medium at a second area, and that is measured by the detector on a second side of the color-measurement medium that is opposite to the first side; and determine a respective transmissive measurement for the first light-emitting region based on the first calibration radiance measurement and on the first color radiance measurement.

Some embodiments of one or more computer-readable storage media store computer-executable instructions that, when executed by one or more computing devices, cause the one or more computing devices to obtain one or more calibration radiance measurements from a detector, wherein each of the calibration radiance measurements is a measurement of light that is emitted by a respective light-emitting region of a light source on a first side of a calibration medium, that is transmitted through the calibration medium at a respective area of the calibration medium, and that is measured by the detector on a second side of the calibration medium that is opposite to the first side; obtain one or more color radiance measurements from the detector, wherein each of the color radiance measurements is a measurement of light that is emitted by a respective light-emitting region of the light source on a first side of a color-measurement medium, that is transmitted through the color-measurement medium at a respective area of the color-measurement medium, and that is measured by the detector on a second side of the color-measurement medium that is opposite to the first side; and determine one or more transmissive measurements based on the one or more calibration radiance measurements and on the one or more color radiance measurements.

BRIEF DESCRIPTION OF THE DRAWINGS

FIGS. 2A and 2B illustrate an example embodiment of a system for obtaining spectral transmissive measurements for media.

DESCRIPTION

The following disclosure describes certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

Figure 2B:
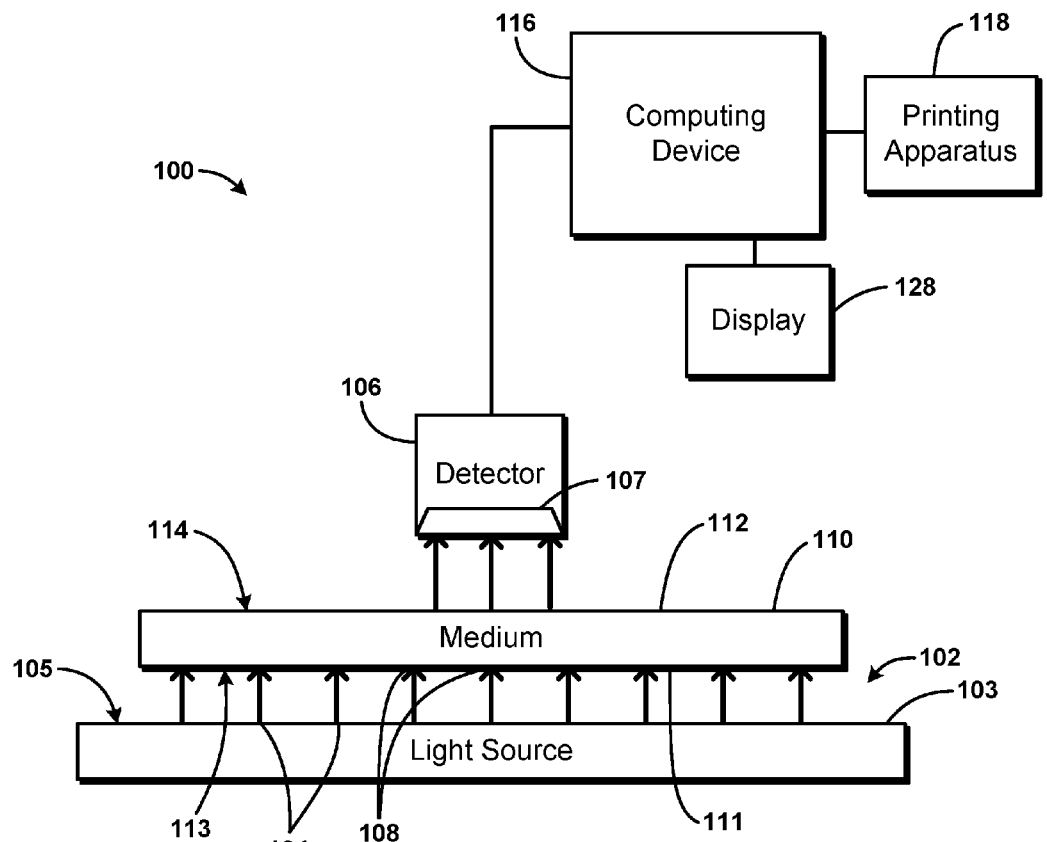
Figure 2B:
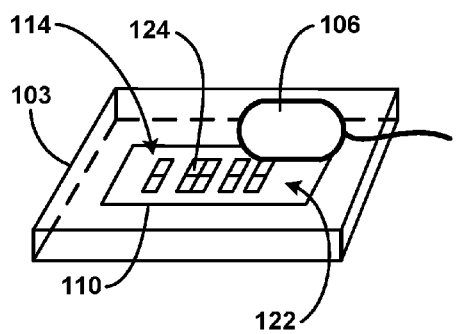
Figure 2C:
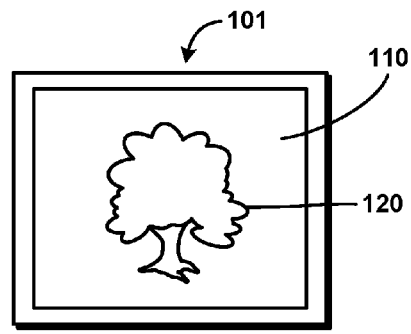
FIG. 2C illustrates an example embodiment of a backlit display.

FIGS. 2A and 2B illustrate an example embodiment of a system 100 for obtaining spectral transmissive measurements for media, which may be used with backlit displays 101. An example embodiment of a backlit display is shown in FIG. 2C. In the embodiment that is illustrated in FIGS. 2A and 2B, the system 100 comprises a light source 102 that includes a plurality of light-emitting regions 104. For example, the light source 102 may be a light panel 103 (e.g., a tablet computer) that emits light from a plurality of light-emitting regions 104 across a two-dimensional surface 105 of the light panel 103. The plurality of light-emitting regions 104 may even form a light-emitting surface that is substantially continuous across the two dimensional surface 105 of the panel 103. The light panel 103 serving as the light source 102 may be of the same type used to illuminate media in a backlit display 101. Examples of such light panels 103 include an edge-lit LED light box that has LEDs formed around the rim of the panel and a diffusion panel that spreads light from the LEDs across the panel, as well as a light panel that has an LED backlighting array. Other light panels or other light sources having other configurations of LEDs, fluorescent lights, or other lighting elements suitable for use in backlit media displays may also be used.

As shown in FIG. 2A, the light source 102 is capable of illuminating a medium 110 that is positioned adjacent to the light source 102, such as on the surface 105 of the light source 102, proximate to the light source 102, or otherwise in the immediate vicinity of the light source 102. The plurality of light-emitting regions 104 emit light that illuminates a plurality of areas 108 on a surface 113 of a first side 111 of the medium 110 that is positioned facing the light source 102. The light that illuminates the plurality of areas 108 is also at least partially transmitted through the medium 110 and can be detected by a detector 106 positioned at a second side 112 of the medium 110 that is opposite to the side 111 of the medium 110 that faces the light source 102.

The detector 106, as shown in FIGS. 2A and 2B, is capable of detecting the transmitted light as a function of wavelength, and may include at least one of a spectrophotometer, a radiometer (e.g., a spectroradiometer), and a spectrally-tunable sensor. For example, the detector 106 can comprise one or more detection elements 107, for example a CCD sensor, a CMOS sensor, a photodiode array for detecting light radiance or light intensity, and a monochromator with a diffraction grating. In some embodiments, the detector 106 is a relatively small hand-held spectrophotometer or the detector is capable of measuring radiance (e.g., spectral radiance). If the detector 106 comprises a spectrophotometer that is capable of measuring in both reflective and emissive modes, then the detector 106 can be operated in an emissive mode (as a spectroradiometer) to obtain the measurements described herein (e.g., without activating a lamp or other light source in the detector 106), such that the light received by the detector 106 is light that is transmitted from the light source 102, as opposed to light that originated from the detector 106 itself.

The detector 106 can be positioned closer to the second side 112 of the medium 110 to received light transmitted through the medium 110. For example, the detector 106 may be positioned such that it rests on a top surface 114 of the medium 110, as shown in the embodiment depicted in FIG. 2B, or may even be positioned a slight distance above the top surface 114 of the medium 110, as depicted in FIG. 2A. The detector 106 generates a signal that describes the detected light.

The detector 106 may also be configured to detect light in a selected wavelength range at a regular step size. For example, some embodiments of the detector 106 can be configured to detect light between the wavelengths of 380 nm and 730 nm using a 10 nm step size.

Figure 1:
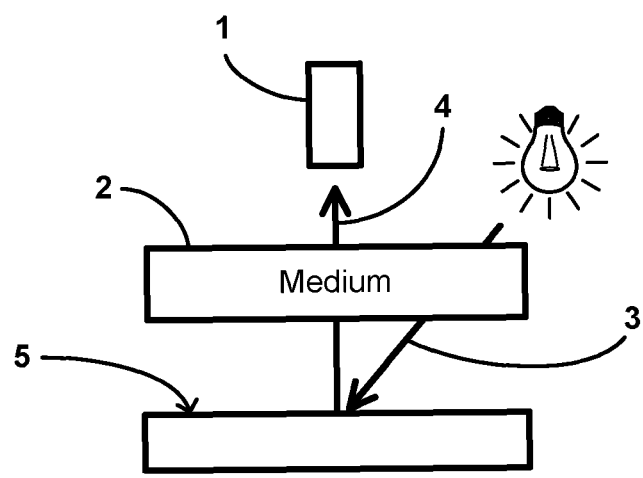
FIG. 1 illustrates a method of obtaining a spectral reflective measurement of a medium.

In contrast to the system in FIGS. 2A and 2B, as shown in FIG. 1 some systems irradiate a printed medium 2 with light 3 and detect the light 4 that is reflected from a surface 5, which is behind the medium 2, back to a detector 1 to obtain a spectral reflectance measurement. Thus, in these systems, light passes through the medium 2 twice as it travels from the light source to the detector 1, and the detector's signal includes a contribution from light that has passed through the medium 2 twice.

Referring again to FIGS. 2A and 2B, the system 100 further comprises a specially-configured computing device 116 that is configured to receive signals from or send signals to the detector 106 and comprises a printing apparatus 118. The computing device 116 is connected to a display 128, such as an LCD monitor or an LED monitor that has a display screen, for displaying information that relates to a process for obtaining spectral transmissive measurements or obtaining color information for printing on media 110 for a backlit display 101. The printing apparatus 118 is capable of printing an image 120 on the medium 110 and can receive a message from the computing device 116 to adjust printing parameters in accordance with color information obtained from a spectral transmissive measurement of a medium. The printing apparatus 118 is configured to use a suitable printing technology for forming images on the medium 110, such as inkjet or laser-printing technologies.

The system 100 can produce spectral transmissive measurements for media 110 that are suitable for use with a backlit display 101. Typically, such media 110 are at least partially translucent or transparent, so that at least a portion of the light emitted by a light source positioned behind the medium 110 passes through and illuminates an image 120 formed on the medium 110, resulting in a vibrant and aesthetically pleasing display to a viewer that observes the image 120 from the front of the display 101. Examples of materials used for media 110 in backlit applications include plastic, glass, plexiglass, film, textile, and even paper that is at least partially transparent or translucent, as well as combinations of such media. Also, each of these materials is an example of a type of media 110.

Because some embodiments of the system 100 illuminate the medium 110 at a plurality of different areas 108, the system 100 allows for a plurality of different transmissive measurements to be obtained in a manner that is relatively easy and convenient for an operator of the system 100. In addition, if the light source 102 is a light panel 103 of the type used for a backlit display 101, then not only can the accuracy of the color information obtained from the transmissive measurements be improved, but also the cost of obtaining color information via the transmissive measurements can be reduced over machines that require specialized light sources and other components.

Figure 3:
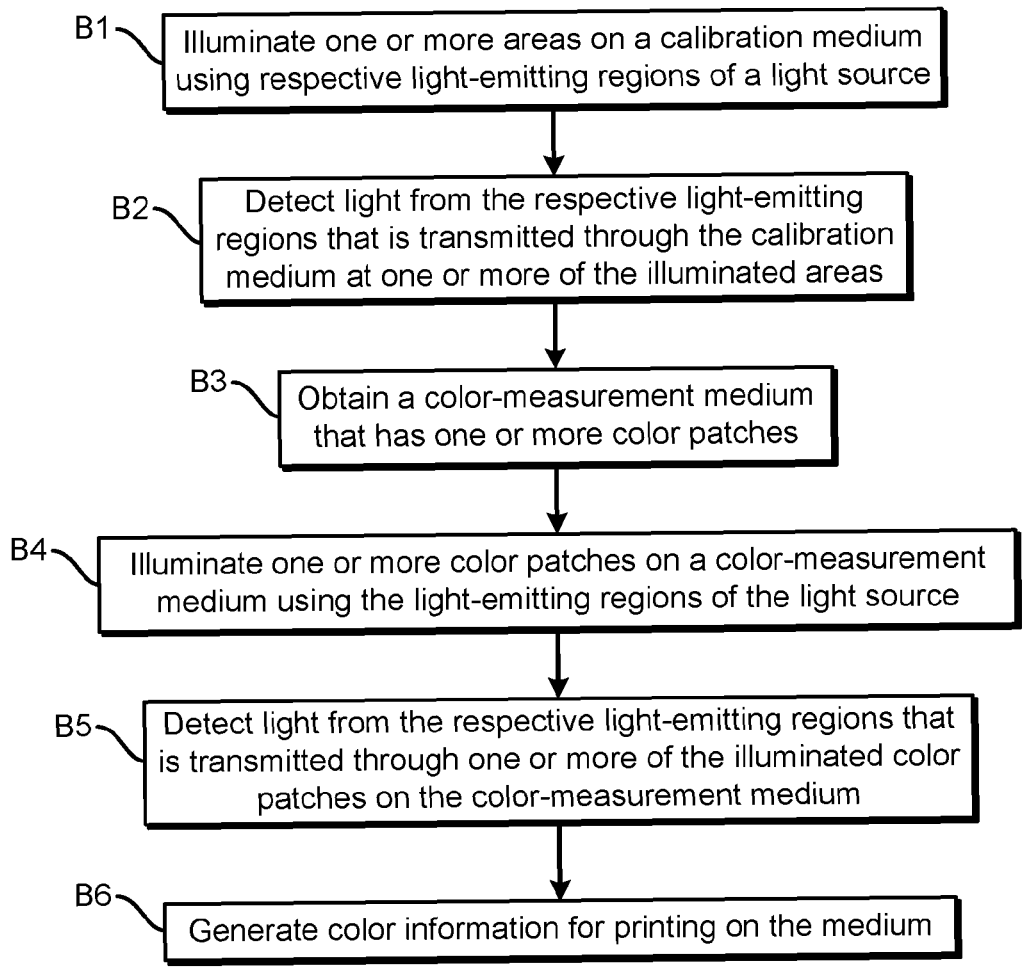
FIG. 3 illustrates an example embodiment of an operational flow for obtaining a spectral transmissive measurement of a medium.

Further details of the system 100 will be explained with reference to the embodiment of an operational flow that is shown in FIG. 3. Although this operational flow and the other operational flows that are described herein are each presented in a certain order, some embodiments of these operational flows perform at least some of the operations in different orders than the presented orders. Examples of possible different orderings include concurrent, overlapping, reordered, simultaneous, incremental, and interleaved orderings. Thus, other embodiments of the operational flows that are described herein may omit blocks, add blocks, change the order of the blocks, combine blocks, or divide blocks into more blocks.

Also, the system 100 may perform the operations in blocks B1-B6 for a particular wavelength, and repeat the operations for other wavelengths. For example, the system 100 may first perform the operations in blocks B1-B6 for light at a wavelength of 450 nm, and then the system 100 may perform the operations in blocks B1-B6 for light at a wavelength of 500 nm. Also, the system 100 may simultaneously perform the operations in blocks B1-B6 for different wavelengths. For example, the system 100 may perform the operations in blocks B1-B6 for light at a wavelength of 450 nm while also performing the operations in blocks B1-B6 for light at a wavelength of 500 nm.

Figure 4A:
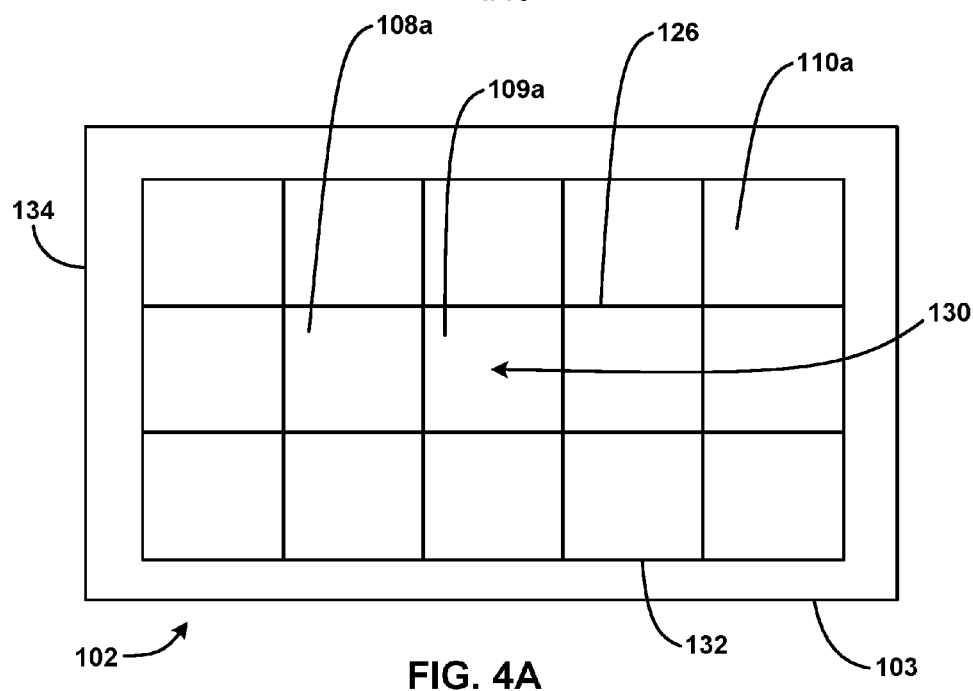
FIGS. 4A and 4B illustrate example embodiments of media.

Starting in block B1, a calibration medium 110a (e.g., as shown in FIG. 4A) is positioned with respect to the light source 102 such that the plurality of areas 108a can be illuminated from the first side 111 of the medium 110a that faces the light source 102 by respective light-emitting regions 104 of the light source 102. If the light source 102 is a light panel 103, then the calibration medium 110a can be placed on the top surface 105 of the light panel 103 to illuminate the plurality of areas 108a via the light-emitting regions 104 immediately below the calibration medium 110a, as shown in FIG. 2A. The calibration medium 110a could alternatively be suspended above the light panel 103. If the light panel 103 comprises a surface 105 that is illuminated continuously or nearly continuously across the two-dimensional surface 105 thereof, such as by a diffusion plate that spreads light throughout the light panel 103, a multi-light array, or another lighting configuration, then the calibration medium 110a may also be substantially illuminated across the entire surface area of the calibration medium 110a. Thus, the plurality of areas 108a illuminated on the calibration medium 110a may form a continuous illuminated area across the calibration medium 110a.

In block B2, the system 100 obtains one or more radiance measurements (e.g., spectral radiance) for the light source 102 and generates calibration-measurement information, which describes the one or more radiance measurements. The radiance measurements that are included in the calibration-measurement information may be referred to herein as calibration radiance measurements. A calibration radiance measurement may be a measurement of the spectral radiance at a light-emitting region 104 of the light source 102. To obtain a calibration radiance measurement, the detector 106 is positioned closer to the second side 112 of the calibration medium 110a than the first side 111 to detect the light from a respective light-emitting region 104 of the light source 102 that is transmitted through the calibration medium 110a at an illuminated area 108a.

For each measured area 108a, the detected light corresponds to the light emitted by the particular light-emitting region 104 that illuminates that area 108a. Thus, the calibration radiance measurement is related to the light emission of the particular light-emitting region 104 of the light source 102. The detector 106 may be positioned to detect light that is transmitted through one or more areas 108a on the calibration medium 110a, and the position of the detector 106 relative to the calibration medium 110a may also be changed to sequentially obtain respective calibration radiance measurements for a plurality of different areas 108 and their respective light-emitting regions 104. For example, in embodiments where the detector 106 is a hand-held spectrophotometer operating in an emissive mode, a user can move the detector 106 across the surface 114 of the calibration medium 110a to sequentially obtain respective a calibration radiance measurement for each of the plurality of different areas 108a and their respective light-emitting regions 104. In some embodiments, the system 100 prompts the user to move the detector 106 to a first area 108a and then sweep the detector 106 across the first area 108a and one or more additional areas 108a, and the system 100 obtains the measurements as the detector 106 is swept across the areas 108a. Also, in some embodiments, the system 100 moves the detector 106 across the surface 114 of the calibration medium 110a.

The computing device 116 receives and stores the calibration-measurement information, which describes the calibration radiance measurements. In some embodiments, the computing device 116 stores the respective calibration-measurement information of each area 108a of the calibration medium 110a for which light passing through the calibration medium 110a is detected. Also, in some embodiments, the calibration-measurement information is stored in the detector 106 itself, for example in a memory or other storage in the detector 106, or the calibration-measurement information is stored in another suitable storage device. If the calibration-measurement information is transferred from the detector 106 to the computing device 116 or another storage device, such transmission can occur by means of any suitable connection, such as a wired connection or a wireless connection.

Thus, in some embodiments, the detector 106 is operated to obtain calibration radiance measurements for light that is transmitted through a plurality of the areas 108a on the calibration medium 110a, and the calibration radiance measurements describe the light that is emitted from a plurality of light-emitting regions 104 of the light source 102. Because the light emitted by the plurality of light-emitting regions 104 is detected when obtaining the calibration radiance measurements, the calibration radiance measurements can be used to ascertain non-uniformities in light emission that occur across the light-emitting regions 104 of the light source 102. For example, if the light source 102 is a light panel 103, the calibration radiance measurements can collectively describe any non-uniformity in the radiance of the light that is emitted by the light panel 103 across the surface 105 of the panel. Such non-uniformities can arise, for example, from a non-uniform diffusion of light across the light panel 103 or other non-uniformities inherent in the manufacture or use of the light source 102.

Additionally, in some embodiments the detector 106 obtains a calibration radiance measurement for light transmitted through only a single area 108a of the plurality of illuminated areas 108a on the calibration medium 110a, which is also a calibration radiance measurement for only that light-emitting region 104 that illuminates the single area 108a. The calibration radiance measurement of the single area 108a can be stored and used to generate a transmissive measurement for a printed medium 110 at that same area 108a, or may be applied to generate transmissive measurements across a plurality of different areas 108a of the medium 110a. A calibration radiance measurement of just a single area 108a of the calibration medium 110a may be suitable, for example, when the light source 102 that is used to illuminate the calibration medium 110a produces uniform light emissions at the plurality of light-emitting regions 104, such that measurement of each individual light-emitting region 104 is not required.

Figure 4B:
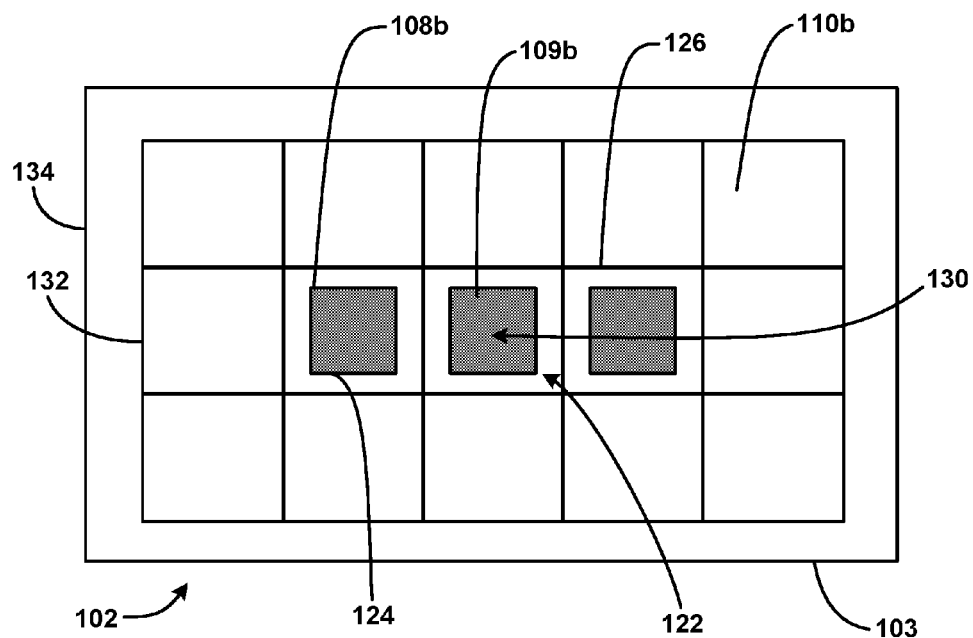

In block B3 of FIG. 3, a color-measurement medium 110b (e.g., as shown in FIG. 4B) is obtained. The color-measurement medium 110b has a color swatch 122 that includes one or more color patches 124 printed thereon. The color patches 124 may each have one of a plurality of different colors that can be printed by the printing apparatus 118, and can collectively include a sufficient number of different colors for color calibration or color-profile creation to be performed for printing on a type of medium 110 with the printing apparatus 118, based on the measurement of the patches 124. In some embodiments, the color-measurement medium 110b is the same medium as the calibration medium 110a that was used to obtain the calibration-measurement information. For example, the calibration medium 110a may itself be printed with the color swatch 122 after the calibration-measurement information has been obtained, such that it can also serve as the color-measurement medium 110b. In some embodiments, a different medium that is the same type of medium as the calibration medium 110a is used as the color-measurement medium 110b; thus, in these embodiments the calibration medium 110a and the color-measurement medium 110b are instances of the same type of medium. And in some embodiments, different media 110 of the same type are printed with one or more color patches 124, thereby producing multiple color-measurement media 110b.

In block B4 of FIG. 3, to obtain the color-measurement information for the color swatch 122, the color-measurement medium 110b is positioned relative to light-emitting areas 104 of the light source 102 such that a plurality of areas 108b of the color-measurement medium 110b are illuminated from a first side 111 of the color-measurement medium 110b that faces the light source 102. In some embodiments, the light source 102 is the same light source that was used to obtain the calibration-measurement information. The color-measurement medium 110b is positioned relative to the light source 102 such that the one or more color patches 124 are aligned with the same light-emitting region 104 that was used to illuminate a corresponding area 108a on the calibration medium 110a when obtaining the calibration-measurement information. Thus, if the light source 102 is a light panel 103, the one or more color patches 124 are aligned on the surface 105 of the light panel 103 at positions on the surface 105 that correspond to where calibration radiance measurements were obtained for one or more areas 108a of the calibration medium 110a. In this way, the color-measurement information that will be obtained for the one or more color patches 124 will correspond to the positions on the surface 105 of the panel 103 where the calibration-measurement information was obtained, such that calibration can be performed across the surface 105.

In block B5 of FIG. 3, radiance measurements of the color patches 124 (also referred to herein as color radiance measurements), which are described by color-measurement information, are obtained by detecting light that is transmitted through at least one of the one or more color patches 124 printed on the color-measurement medium 110b, from a second side 112 of the color-measurement medium 110b that is opposite the first side 111 that faces the light source 102.

The detector 106 is positioned to detect light that is transmitted through one or more of the color patches 124 that are illuminated by the light-emitting regions 104 of the light source 102. While the color-measurement medium 110b is aligned relative to the light source 102 such that respective positions of one or more color patches 124 correspond to the one or more areas 108a of the calibration medium 110a for which calibration radiance measurements were obtained, the detector 106 obtains color radiance measurements by detecting the light that is transmitted through one or more color patches 124 that correspond to the areas 108a of the calibration medium 110a. The position of the detector 106 relative to the color-measurement medium 110b may be changed to sequentially obtain the color radiance measurements for a plurality of different color patches 124. In some embodiments, a plurality of different color patches 124 on the color-measurement medium 110b are sequentially measured by the detector 106, with the color patches 124 each being aligned at a position that corresponds to an area 108*a* of the calibration medium 110*a* that was measured when obtaining the calibration radiance measurements.

Alternatively, the plurality of color patches 124 can be positioned with respect to the light source 102 without regard to any prior alignment of the areas 108*a* on the calibration medium 110*a*. For example, alignment of the color patches 124 with the previous positions of the areas 108*a* on the calibration medium 110*a* may not be used when light emissions from a light panel 103 are uniform across the surface 105 of the light panel 103 such that a calibration radiance measurement from only a single light-emitting region 104 of the panel 103 is required for accurate transmissive measurements.

The operations that are performed to obtain the color radiance measurements with the detector 106 can be the same as or similar to the operations described above in block B2 for obtaining the calibration radiance measurements. As described above, the detector 106 may a hand-held type and may be operated either by positioning the detector 106 directly on the surface 114 of the color-measurement medium 110*b* or by holding the detector 106 at a position above the color-measurement medium 110*b*. In some embodiments, the system 100 prompts the user to move the detector 106 to a first area 108*b* and then sweep the detector 106 across the first area 108*b* and one or more additional areas 108*b*, and the system 100 obtains the color radiance measurements as the detector 106 is swept across the areas 108*b*. Also, in some embodiments the system 100 moves the detector 106 across the surface 114 of the color-measurement medium 110*b*.

Additionally, in some embodiments, a plurality of color patches 124 printed on the color-measurement medium 110*b* are sequentially aligned relative to the light source 102 to sequentially align each of the color patches 124 at a single position that corresponds to an area 108*a* that was illuminated by a single light-emitting region 104 when a calibration radiance measurement was obtained. For example, if a light source 102 includes a light panel 103, then the plurality of color patches 124 can be positioned such that light is detected through a single color patch 124 that is aligned with the single position on the surface 105 of the panel 103 of the single light-emitting region 104 that was used to obtain the calibration radiance measurement. The position of the color patches 124 can then be moved, such as by moving the medium 110*b* along the surface 105 of the panel 103, to re-align a new color patch 124 at the position and obtain the color radiance measurement for the new color patch 124.

Also, in some embodiments the plurality of color patches 124 are printed on multiple color-measurement media 110*b* of the same type, and the color radiance measurement for each color patch 124 printed on each color-measurement medium 110*b* can be obtained by sequentially positioning each color-measurement medium 110*b* to detect the light transmitted through the color patch 124, thereby obtaining the color radiance measurement for that color patch 124, and subsequently repeating the measurement for the other measurement media 110*b* that have the color patches 124 printed thereon, until respective color radiance measurements for the color patches 124 printed on each of the plurality of measurement media 110*b* have been obtained. While the detection of light transmitted through a plurality of color patches 124 may be required to obtain certain color information, for example color information used to create a color profile, in some embodiments it is possible to obtain color radiance measurements from only a single patch 124 on the color-measurement medium 110*b*.

The color radiance measurements obtained while detecting light transmitted through one or more of the patches 124 can also be stored, similar to the calibration radiance measurements, for use in determining transmissive measurements. For example, the detector 106 can generate a signal that describes the detected color radiance measurements and that is transmitted to a computing device 116 for storage, or another storage method may be used that is the same as or similar to that discussed for the storage of the calibration radiance measurements.

Finally, in block B6, once the calibration radiance measurements and the color radiance measurements have been obtained, the computing device 116 generates the color information for printing with the printing apparatus 118 on the media 110 based on a relationship between the calibration radiance measurements and the color radiance measurements. However, in some embodiments, the color information is generated by the detector itself 106, and the detector 106 can generate a signal that describes the determined color information to send to the computing device 116. Also, in some embodiments, generating the color information includes generating a transmissive measurement, of the instance of the medium or the type of the medium, based on the calibration-measurement information and the color-measurement information. In some embodiments, the transmissive measurement is a transmittance-factor measurement or a transmissive-density measurement.

For example, if the calibration-measurement information describes a spectral radiance of light transmitted through the calibration medium 110*a*, and the color-measurement information describes a spectral radiance of light transmitted through the color-measurement medium 110*b*, then a transmittance-factor measurement can be determined on a wavelength-by-wavelength basis according to the following:

$$TF(\lambda) = \frac{T_m(\lambda)}{T_c(\lambda)}, \qquad \text{equation (1)}$$

where $TF(\lambda)$ is the transmittance-factor measurement at wavelength $\lambda$, where $T_m(\lambda)$ is the color radiance measurement (e.g., spectral radiance) that was obtained from detecting light of wavelength $\lambda$ that was transmitted through at least one color patch 124 on the color-measurement medium 110*b*, and where $T_c(\lambda)$ is the calibration radiance measurement (e.g., spectral radiance) that was obtained from detecting light of wavelength $\lambda$ that was transmitted through the calibration medium 110*a*.

Also for example, a transmissive-density measurement can be determined on a wavelength-by-wavelength basis according to the following:

$$TD(\lambda) = -\log_{10}\left(\frac{T_m(\lambda)}{T_c(\lambda)}\right), \qquad \text{equation (2)}$$

where $TD(\lambda)$ is the transmissive-density measurement at wavelength $\Delta$, where $T_m(\lambda)$ is the color radiance measurement (e.g., spectral radiance) that was obtained from detecting light of wavelength $\lambda$ that was transmitted through at least one color patch 124 that was printed on the color-measurement medium 110*b*, and where $T_c(\lambda)$ is the calibration radiance measurement (e.g., spectral radiance) that was obtained from detecting light of wavelength $\lambda$ that was transmitted through the calibration medium 110*a*.

For both transmittance-factor TF(λ) and transmissive-density TD(λ) measurements, the color radiance measurement $T_m(\lambda)$ and the calibration radiance measurement $T_c(\lambda)$ may be values for a wavelength that were acquired at a particular position of the media 110 that corresponds to the same light-emitting region 104 of the light source 102. Thus, each color radiance measurement $T_m$ and calibration radiance measurement $T_c$ value may be a measurement that was taken at the same light-emitting region 104 of the light-emitting regions 104 of the light source 102. Also, a single calibration radiance measurement $T_c$ obtained for one position on the media 110 can be used for calibration of a plurality of color radiance measurements $T_m$ taken at different positions.

Typically the transmittance factor (TF) color information can be used to perform color management for printing on the type of the media 110 using the printing apparatus 118, for example to create a color profile and perform color calibration for printing on the type of the media 110 with the printing apparatus 118. A color profile is a set of data that characterizes a color output by a printer or other printing apparatus, such as by defining a mapping to a profile connection space (PCS). The color profile can thus allow for colors in an image generated on one device, for example a computing device, to be accurately reproduced by an output device, such as the printing apparatus 118, by converting a color used in the color representation in one device to the corresponding color in the color representation used in the other device. That is, the color profiles can be used to ensure that a color of an image on one device is the same as that on another device. A number of different color profile standards have been promulgated by the International Color Consortium (ICC), referred to as ICC profiles, and device-link profiles that directly link the color spaces of certain devices also exist. The color profile depends upon factors such as the particular model and type of printing apparatus being used, the type of media to be printed on, and the types of inks or other colorants being used for printing.

Accordingly, when printing on a particular type of media, a color profile can be created for printing on the type of media with the particular printing apparatus that is being used to provide accuracy in the color output by the printing apparatus. By creating the color profile, the parameters for color printing that are used by the printing apparatus 118 can be adjusted to provide the correct color output. For example, for a printing apparatus 118 that uses ink-jet printing technology, the contents of an ink color can be modified with respect to other ink color contents in accordance with the color-profile parameters to provide for accurate color output by the printing apparatus 118.

Color calibration using transmissive-density (TD) measurements can also be used to adjust the output of a printing apparatus 118 based on the obtained color information. For example, color calibration can be performed to adjust the color printed by the printing apparatus 118 to compensate for changes that can occur over time to the color output and changes to the color output that are due to environmental conditions, such as humidity, temperature, etc.

In some embodiments, the system 100 is configured to help a user properly align one or more of the calibration medium 110a and the color-measurement medium 110b with respect to the light source 102, to provide proper calibration and color measurement for the media 110. At least one of the calibration medium 110a and the color-measurement medium 110b may be provided with alignment markings 126 that can help a user (or a device) properly align one or more of the media 110 relative to the light source 102 or the detector 106.

FIG. 4A shows a calibration medium 110a that has alignment markings 126 thereon and that is positioned on a light source 102 (e.g., on the surface 105 of a light panel 103). The calibration-measurement information can then be obtained by detecting the light transmitted through one or more areas 108a of the calibration medium 110a that are delineated or otherwise defined or signified by the alignment markings 126. That is, a user or a device can use the alignment markings 126 to identify a predetermined position 109a on the calibration medium 110a and can position the detector 106 relative to the predetermined position 109a to obtain a calibration radiance measurement. Calibration-measurement information for additional predetermined positions 109a can also be obtained by re-positioning the detector 106 in accordance with the alignment markings 126, which identify other areas 108a for calibration measurement.

Referring to FIG. 4B, the color-measurement medium 110b can similarly be printed with alignment markings 126 to identify predetermined positions 109b that correspond to the positions 109a for which calibration-measurement information was obtained. Thus, as shown in FIG. 4B, the color-measurement medium 110b can be printed with a plurality of color patches 124 as well as alignment markings 126 that identify the positions of the color patches 124. A user or device can use the alignment markings 126 to identify patches 124 in predetermined positions 109b that correspond to the positions 109a for which a calibration radiance measurement was obtained, such that transmissive measurements for those same positions 109b can be obtained. Because the positions 109a of the calibration medium 110a and the positions 109b of the color-measurement medium 110b correspond to a particular position relative to the light source 102, such as a particular position on a surface 105 of a light panel 103, the alignment markings 126 provide a means by which calibration radiance measurements that can be used to compensate for non-uniformities across the light source 102 can be obtained.

While the alignment markings 126 depicted in FIGS. 4A and 4B are grid-like markings, other types of alignment markings could also be used, such as letters or numbers that identify a particular position on the media 110. Other information that may be useful to a user or a detector, such as directions that describe a sequence for obtaining the transmissive measurements, could also be printed on the media 110. The alignment markings 126 could be printed by the same printing apparatus 118 for which color information is being obtained. Also, the alignment markings 126 could be pre-printed in advance on media that are for use with the system 100.

Figure 5:
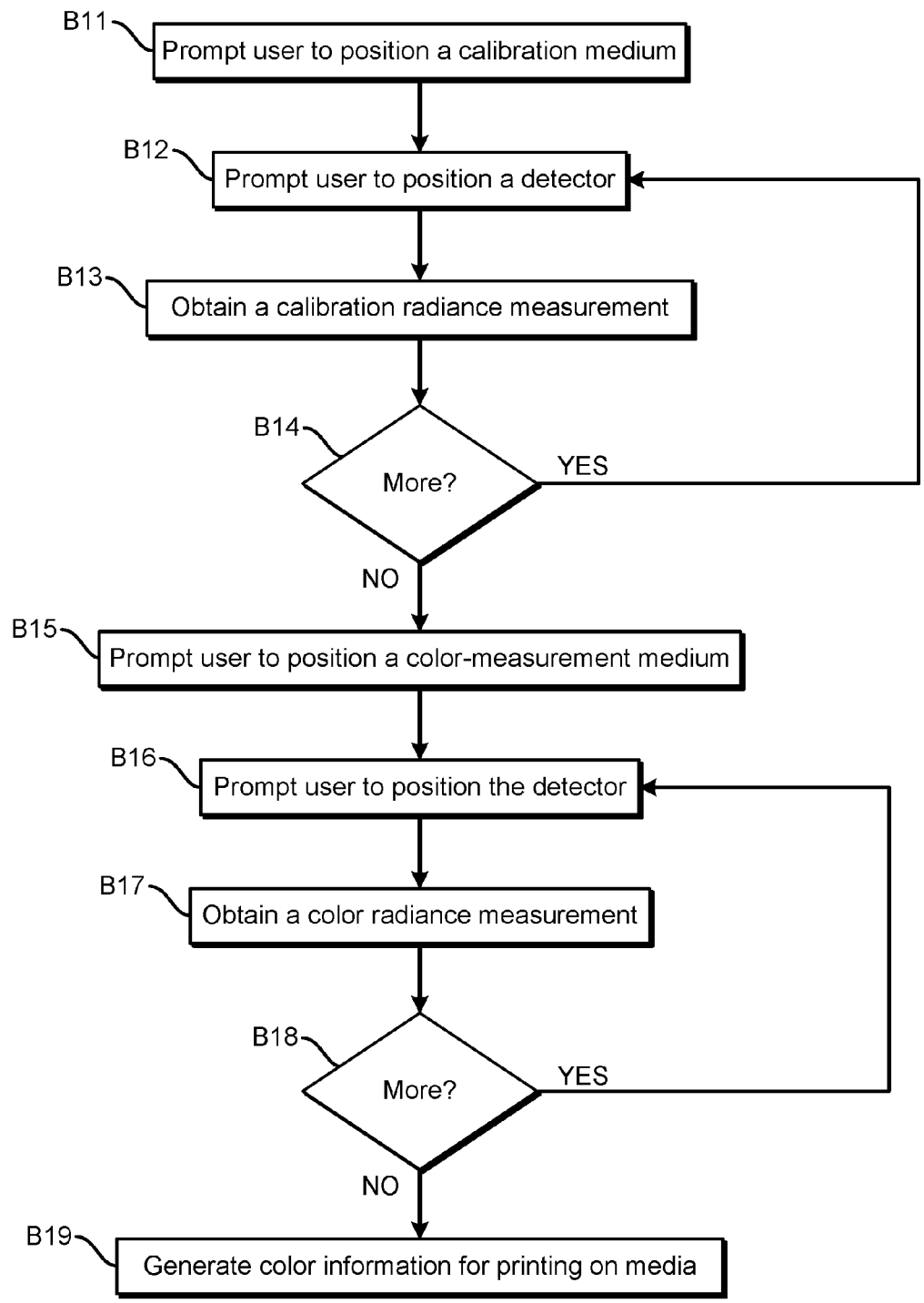
FIG. 5 illustrates an example embodiment of an operational flow for obtaining a spectral transmissive measurement of a medium.

In some embodiments, the system 100 is configured to provide an interactive process for obtaining a spectral transmissive measurement of a medium or color information. FIG. 5 illustrates an example embodiment of an operational flow for obtaining a spectral transmissive measurement of a medium. This operational flow may be performed by the system 100 in FIG. 2 or by other specially-configured systems (e.g., the system 1300 in FIG. 13).

Additionally, the system 100 may perform the operations in blocks B11-B19 for a particular wavelength and also perform the operations for other wavelengths, either sequentially or simultaneously. For example, the system 100 may first perform the operations in blocks B11-B19 for light at the wavelength of 400 nm, and then the system 100 may perform the operations in blocks B11-B19 for light at the wavelength of 460 nm. Also, the system 100 may perform the operations in blocks B11-B19 for light at the wavelength of 400 nm while also performing the operations in blocks B11-B19 for light at the wavelength of 460 nm. And the measurements may be repeated and averaged to obtain average measurements.

First, in block B11, the system 100 prompts a user to position a calibration medium (e.g., the calibration medium 110a in FIG. 4A) relative to a light source 102, which has a plurality of light-emitting regions 104. In embodiments where the calibration medium 110a has alignment markings 126 thereon, a user may be prompted to position the calibration medium 110a such that the alignment markings 126 are aligned at a predetermined position relative to the light source 102. For example, if the light source 102 is a light panel 103, the user may be prompted to align the calibration medium 110a at a center 130 of the light source 102, to align a particular position 109a of the calibration medium 110a with a position on the light panel 103, or to align an edge 132 of the calibration medium 110a along an edge 134 of the light panel 103. The user can be prompted by presenting instructions on a display 128 of the computing device 116, by audio instructions, or by other means of communicating with the user. In some embodiments, the display 128 of the computing device 116 displays instructions for aligning the calibration medium 110a, such as by displaying instructions, diagrams, or videos that depict the proper placement. Also for example, the display 128 may depict an illustration of a calibration medium 110a that is properly positioned with respect to a light source 102 (e.g., a light panel 103) as a guide to the user for positioning the calibration medium 110a.

Next, in block B12, the user is prompted to position the detector 106 relative to the calibration medium 110a, for example relative to the alignment markings 126, such that calibration-measurement information can be obtained for a predetermined position 109a on the calibration medium 110a. Similar to block B11 described above, the user can be prompted via instructions, diagrams, videos, or other audio or visual means. If a hand-held detector 106 is used, then the user can be prompted to move the detector 106 to a predetermined position 109a that is indicated by the alignment markings 126 so that a calibration radiance measurement for the area 108a corresponding to the predetermined position 109a can be obtained. For example, the user can be prompted to position the detector 106 by displaying, on the display 128, grid coordinates for alignment markings 126 that are in the form of a grid to guide a user to position the detector 106 with respect to the grid coordinates. The user can also be prompted by displaying a label on the display 128 that corresponds to an alignment marking 126 of a particular position 109a on the calibration medium 110a or by depicting an illustration of the detector 106 properly positioned relative to the calibration medium 110a.

In some embodiments, the detector 106 is configured to detect the alignment markings 126 and to provide a signal in response to such detection that can be used to further help a user (or a device) align the calibration medium 110a for calibration radiance measurements. For example, the detector 106 may generate a signal in response to the detection of the alignment markings 126 that can be provided to the computing device 116 for use in determining a position of the detector 106 relative to the alignment markings 126, such that the computing device 116 can generate further instructions for aligning the detector 106 with the calibration medium 110a.

In block B13 of FIG. 5, once the detector 106 has been properly aligned with the predetermined position 109a on the calibration medium 110a, the system 100 obtains the calibration radiance measurement for the area 108a at the predetermined position 109a. For example, the user may press a button on the detector 106 to initiate detection of light that is transmitted through the calibration medium 110a at the area 108a, or the user may select an option to initiate detection via a keyboard, a mouse, or another input to the computing device 116. In embodiments where the detector 106 can itself detect the alignment markings 126 and transmit a signal in response to the detection to the computing device 116, the computing device 116 may also be configured to generate a signal for transmission to the detector 106 to cause the detector 106 to initiate detection once the proper alignment has been recognized. A signal generated by the detector 106 that describes the detected calibration radiance measurement can be obtained by the computing device 116 or another location for storage or processing of the detected calibration radiance measurement, and the calibration radiance measurement can be stored or processed by the detector 106 itself.

In block B14, a determination is made as to whether or not a calibration radiance measurement should be obtained for another position 109a corresponding to another illuminated area 108a of the calibration medium 110a. The determination can be made, for example, according to a pre-determined scheme for obtaining the calibration radiance measurements, such as a scheme that dictates the number and positions of calibration radiance measurements to be taken with the calibration medium 110a. For example, the computing device 116 may be capable of determining whether the complete number of calibration radiance measurements has been taken according to the pre-determined scheme or whether subsequent measurements are still required. If it is determined that more calibration radiance measurements are required (Yes in block B14), then the flow returns to block B12, and the user is again prompted to move the detector 106 to a new position 109a on the calibration medium 110a to obtain a subsequent calibration radiance measurement. If it is determined that sufficient calibration radiance measurements have been obtained (No in block B14), then the operational flow moves to block B15.

In block B15, the user is prompted to position a color-measurement medium 110b relative to the light source 102. The user may be prompted via the display 128 to position the color-measurement medium 110b relative to the light source 102 such that one or more color patches 124 that are printed on the color-measurement medium 110b are aligned with positions 109a of the calibration medium 110a where the calibration radiance measurements were obtained. Thus, the color patches 124 may be positioned relative to the light source 102 such that each color patch 124 is illuminated by a light-emitting region 104 that previously illuminated a corresponding area 108a for which a calibration radiance measurement was obtained. Similar to the operations described above, the user can be prompted via instructions, diagrams, videos, or other audio or visual means, including instructions shown on a display 128 of the computing device 116. For example, the user may be prompted to align the color-measurement medium 110b relative to the light source 102 using the alignment markings 126. Also for example, the alignment markings 126 can be used to position the color patches 124 of the color-measurement medium 110b over the same light-emitting regions 104 that illuminated the calibration medium 110a while obtaining the calibration-measurement information. In some embodiments, the display 128 of the computing device 116 displays instructions for alignment of the color-measurement medium 110b, such as by displaying instructions, diagrams, or videos that depict the proper placement, or by other means of instruction. For example, the display 128 may depict an illustration of a color-measurement medium 110b that is properly positioned relative to a light panel 103 or other light source 102, as a guide to the user for positioning the color-measurement medium 110b.

In block B16, system 100 prompts the user to position the detector 106 relative to the color-measurement medium 110b, for example relative to the alignment markings 126, such that a color radiance measurement can be obtained for a color patch 124 at a particular position 109b on the color-measurement medium 110b. Similar to the operations described above, the system 100 can prompt the user via instructions, diagrams, videos, or other audio or visual means, including instructions shown on a display 128 of the computing device 116. If a hand-held detector 106 is used, the user can be prompted to move the detector 106 to a predetermined position 109b that is identified by the alignment markings 126 and that corresponds to a position 109a of the calibration medium 110a where a calibration radiance measurement was obtained, so that a color radiance measurement for the area 108b corresponding to the predetermined position 109b can be obtained. For example, the system 100 can prompt the user to position the detector 106 by showing, on the display 128, grid coordinates for alignment markings 126 in the form of a grid to guide a user to position the detector 106 with respect to the grid coordinates. The user can also be prompted by displaying a label on the display 128 that corresponds to an alignment marking 126 that is for a particular position 109a on the color-measurement medium 110b or by depicting an illustration of the detector 106 properly positioned relative to the color-measurement medium 110b. Similar to block B12 above, the detector 106 may itself also be configured to detect the alignment markings 126 and to provide a signal in response to such detection that can be used to further help the user align the color-measurement medium 110b. For example, the detector 106 may generate a signal in response to detecting the alignment markings 126 that can be provided to the computing device 116 for use in determining a relative position of the detector 106 with respect to the alignment markings 126, such that the computing device can generate further instructions for aligning the detector 106 with the color-measurement medium 110b.

Once the proper alignment of the color-measurement medium 110b and the detector 106 has been attained, in block B17 the system 100 obtains the color radiance measurement for the area 108b corresponding to the predetermined position 109a. For example, the user may press a button on the detector 106 to initiate detection of light transmitted through the color-measurement medium 110b at the color patch 124 corresponding to the area 108b or may select an option to begin detection via a keyboard, mouse, or other input to the computing device 116. In embodiments where the detector 106 can detect the alignment markings 126 and transmit a signal in response to the detection to the computing device 116, the computing device 116 may also be capable of transmitting a signal to the detector 106 to cause the detector 106 to initiate detection once the proper alignment has been recognized. A signal generated by the detector 106 that describes the detected color radiance measurement can be received by the computing device 116 or transmitted to another location for storage or processing of the detected color radiance measurement, or the color radiance measurement can be stored or processed by the detector 106 itself.

Next, in block B18, the system 100 determines whether a color radiance measurement should be obtained for another color patch 124 at another position 109b corresponding to another illuminated area 108b of the color-measurement medium 110b. The determination can be made, for example, according to a pre-determined scheme for obtaining the color radiance measurements, such as a scheme dictating the number and position of color radiance measurements to be taken with the color-measurement medium 110b relative to the number of calibration radiance measurements taken or other criteria. For example, the computing device 116 may determine whether the complete number of color radiance measurements has been taken according to the pre-determined scheme for determining color information, or whether subsequent color radiance measurements are still required. In some embodiments, the number of color radiance measurements taken corresponds to at least one color radiance measurement for each calibration radiance measurement taken at each position 109a of the calibration medium 110a. Thus, the user may be prompted to re-align the detector 106 with respect to the color-measurement medium 110b a plurality of times to obtain a plurality of color radiance measurements for different areas 108b on the color-measurement medium 110b. If it is determined that more color radiance measurements are required (Yes in block B18), then the operational flow returns to block B16, and system 100 again prompts the user to align the detector 106 with a new position 109b on the color-measurement medium 110b. Alternatively, if in block B18 it is determined that more color radiance measurements are required, then the flow may also return to block B15 to prompt the user to re-position the color-measurement medium 110b relative to the light source 102, depending on the scheme for obtaining the color information that is being used. The flow may also return to block B15 to prompt the user to position a new color-measurement medium having different color patches 124 printed thereon to obtain color radiance measurements for this different color-measurement medium 110b. If it is determined that sufficient color radiance measurements have been obtained (No in block B18), then the operational flow moves on to block B19.

In block B19, the color information (e.g., a transmissive measurement) for printing on media is determined based on the calibration radiance measurements information that were obtained in block B13 and on the color radiance measurements that were obtained in block B17. The color information can be used to create a color profile for the printing apparatus 118 that was used to print the color patches 124 on the color-measurement medium 110b, to calibrate the color used by the printing apparatus 118 in printing on the media 110, or to otherwise perform color management for the printing apparatus 118 in the printing of images 120 on media 110.

Figure 6:
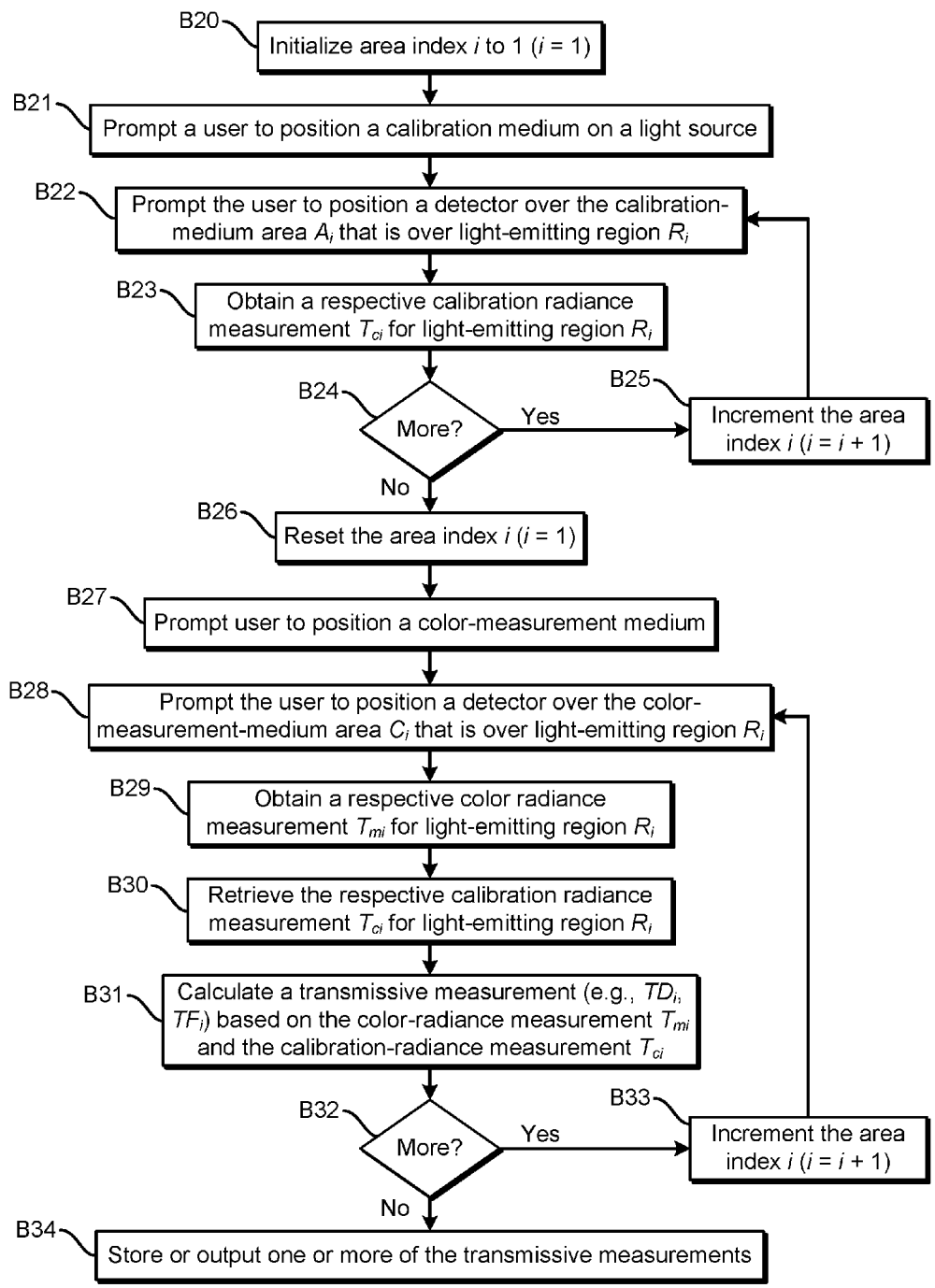
FIG. 6 illustrates an example embodiment of an operational flow for obtaining spectral transmissive measurements of a medium.

FIG. 6 illustrates an example embodiment of an operational flow for obtaining spectral transmissive measurements of a medium. The operational flow may be performed by the system 100 in FIG. 2, the system 1300 in FIG. 13, or another specially-configured system. Additionally, the operations in blocks B20-B34 can be performed for a particular wavelength and also performed, either simultaneously or sequentially, for other wavelengths. For example, the system 100 may first perform the operations in blocks B20-B34 for light at the wavelength of 650 nm, and then the system 100 may perform the operations in blocks B20-B34 for light at the wavelength of 640 nm. Also, the system 100 may perform the operations in blocks B20-B34 for light at the wavelength of 650 nm while performing the operations in blocks B20-B34 for light at the wavelength of 640 nm. And the measurements may be repeated and averaged to obtain average measurements.

The flow begins in block B20, where an area index i is initialized to one. Next, in block B21, the system (e.g., a computing device and a display in the system) prompts a user to position a calibration medium on a light source, which includes light-emitting regions. The flow then moves to block B22, where the system prompts the user to position a detector over the calibration-medium area $A_i$ (e.g., the area 108a in FIG. 4A) that is over light-emitting region $R_i$. Next, the system obtains and stores a respective calibration radiance measurement $T_{c_i}$ for light-emitting region $R_i$.

The flow then moves to block B24, where the system determines if another calibration radiance measurement should be obtained. If yes (Yes in block B24), then the flow moves to block B25, where the area index i is incremented, and then the flow returns to block B22. If not (No in block B24), then the flow moves to block B26.

In block B26, the area index i is reset to 1. Next, in block B27, the system prompts the user to position a color-measurement medium. The flow then moves to block B28, where the system prompts the user to position a detector over the color-measurement-medium area $C_i$ (e.g., the area 108b in FIG. 4B) that is over light-emitting region $R_i$. The flow then proceeds to block B29, where the system obtains a respective color radiance measurement $T_{m_i}$ for light-emitting region $R_i$. Next, in block B30, the system retrieves the respective calibration radiance measurement $T_{c_i}$ for light-emitting region $R_i$, and in block B31 the system calculates a transmissive measurement (e.g., a transmittance-factor measurement $TF(\lambda)$, a transmissive-density measurement $TD(\lambda)$) for light-emitting region $R_i$ based on the color radiance measurement $T_{m_i}$ and the calibration radiance measurement $T_{c_i}$, for example as described by equation (1) or equation (2).

The flow then moves to block B32, where the system determines if another color radiance measurement should be obtained. If yes (Yes in block B32), then the flow moves to block B33, where the area index i is incremented, and then the flow returns to block B28. If not (No in block B32), then the flow moves to block B34. In block B34, the system stores or outputs one or more of the transmissive measurements.

Figure 7:
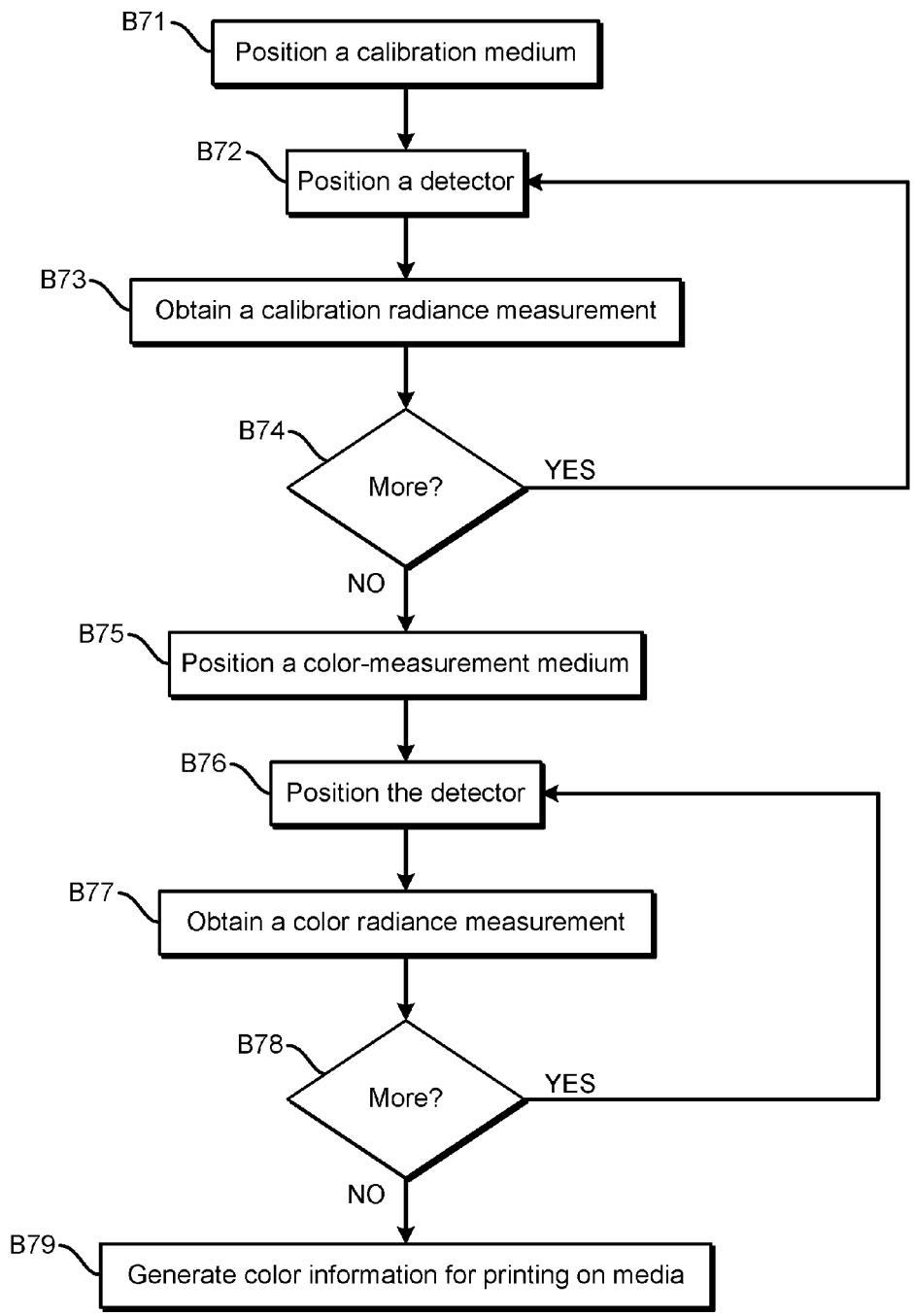
FIG. 7 illustrates an example embodiment of an operational flow for obtaining a spectral transmissive measurement of a medium.

FIG. 7 illustrates an example embodiment of an operational flow for obtaining a spectral transmissive measurement of a medium. This operational flow may be performed by an appropriately-configured embodiment of the system 100 in FIG. 2 or another specially-configured system (e.g., the system in FIG. 13). In this embodiment, the system is configured to automatically position a calibration medium and a detector. Also, the system may respectively perform the operations in blocks B71-B79 for particular wavelengths of light, either sequentially or simultaneously. And the measurements may be repeated and averaged to obtain average measurements.

First, in block B71, the system positions a calibration medium (e.g., the calibration medium 110a in FIG. 4A) relative to a light source, which may have a plurality of light-emitting regions. In embodiments where the calibration medium includes alignment markings, the system may use the alignment markings to position the calibration medium such that the alignment markings are aligned at predetermined positions relative to the light source. For example, if the light source is a light panel, then the system may use the alignment markings to align a particular position of the calibration medium with a position on the light panel or align an edge of the calibration medium along an edge of the light panel.

Next, in block B72, the system positions a detector relative to the calibration medium, for example relative to the alignment markings, such that one or more calibration radiance measurements can be obtained for a predetermined position on the calibration medium.

In some embodiments, the detector is configured to detect the alignment markings and to provide a signal in response to such detection that can be used by the system to align the calibration medium. For example, the detector may generate a signal in response to the detection of the alignment markings that can be provided to the computing device for use in determining a position of the detector relative to the alignment markings.

In block B73, once the detector has been properly aligned with the predetermined position on the calibration medium, the system obtains one or more calibration radiance measurements for the area that is located at the predetermined position. A signal generated by the detector that describes the detected one or more calibration radiance measurements can be obtained by the computing device or another device for storage or processing of the detected one or more calibration radiance measurements, and the one or more calibration radiance measurements can be stored or processed by the detector itself.

In block B74, the system determines whether one or more calibration radiance measurements should be obtained for another position that is located at another illuminated area of the calibration medium. The determination can be made, for example, according to a pre-determined scheme for obtaining the calibration radiance measurements, such as a scheme that dictates the number and positions of calibration radiance measurements to be taken with the calibration medium. For example, the computing device may be capable of determining whether the complete number of calibration radiance measurements has been taken according to the pre-determined scheme or whether additional calibration radiance measurements are still required. If the system determines that more calibration radiance measurements are required (Yes in block B74), then the flow returns to block B72, and the system moves the detector to a new position on the calibration medium. If the system determines that sufficient calibration radiance measurements have been obtained (No in block B74), then the operational flow proceeds to block B75.

In block B75, the system positions the color-measurement medium relative to the light source. The system may position the color-measurement medium relative to the light source such that one or more color patches on the color-measurement medium are aligned with positions of the calibration medium where the calibration radiance measurements were obtained. Thus, the system may position the color patches relative to the light source such that each color patch is illuminated by a light-emitting region that previously illuminated a corresponding area where a calibration radiance measurement was obtained. Also, the system can use alignment markings to position the color patches of the color-measurement medium over the same light-emitting regions that illuminated the calibration medium while obtaining the calibration-measurement information.

In block B76, the system positions the detector relative to the color-measurement medium, for example relative to the alignment markings, such that one or more color radiance measurements can be obtained for a color patch at a particular position on the color-measurement medium. Similar to block B72 above, the detector may itself be configured to detect the alignment markings and to provide a signal in response to such detection that the system can use to align the color-measurement medium. For example, the detector may generate a signal in response to detecting the alignment markings that can be provided to the computing device for use in determining a position of the detector relative to the alignment markings.

Once the proper alignment of the color-measurement medium and the detector has been attained, in block B77 the system obtains the one or more color radiance measurements for the area at the predetermined position. A signal generated by the detector that describes the detected one or more color radiance measurements can be received by the computing device or transmitted to another device for storage or processing of the detected one or more color radiance measurements, or the one or more color radiance measurements can be stored or processed by the detector itself.

Next, in block B78, the system determines whether one or more color radiance measurements should be obtained for another color patch at a position that is located at another illuminated area of the color-measurement medium. The determination can be made, for example, according to a pre-determined scheme for obtaining the color radiance measurements, such as a scheme dictating the number and position of color radiance measurements to be taken with the color-measurement medium relative to the number of calibration radiance measurements taken or other criteria. For example, the computing device may determine whether the complete number of color radiance measurements has been taken according to the pre-determined scheme for determining color information. In some embodiments, the number of color radiance measurements taken corresponds to at least one color radiance measurement for each calibration radiance measurement taken at each position of the calibration medium. If the system determines that more color radiance measurements are required (Yes in block B78), then the operational flow returns to block B76, and the system aligns the detector with a new position on the color-measurement medium. Alternatively, if the system determines in block B78 that more color radiance measurements are required, then the flow may also return to block B75, where the system re-positions the color-measurement medium relative to the light source. If the flow returns to block B75, then the system may position a new color-measurement medium having different color patches printed thereon to obtain one or more color radiance measurements for this different color-measurement medium. If the system determines that sufficient color radiance measurements have already been obtained (No in block B78), then the operational flow proceeds to block B79.

In block B79, the system determines the color information (e.g., a transmissive measurement) for printing on the type of the medium based on the calibration radiance measurements that were obtained in block B73 and on the color radiance measurements that were obtained in block B77.

Figure 8:
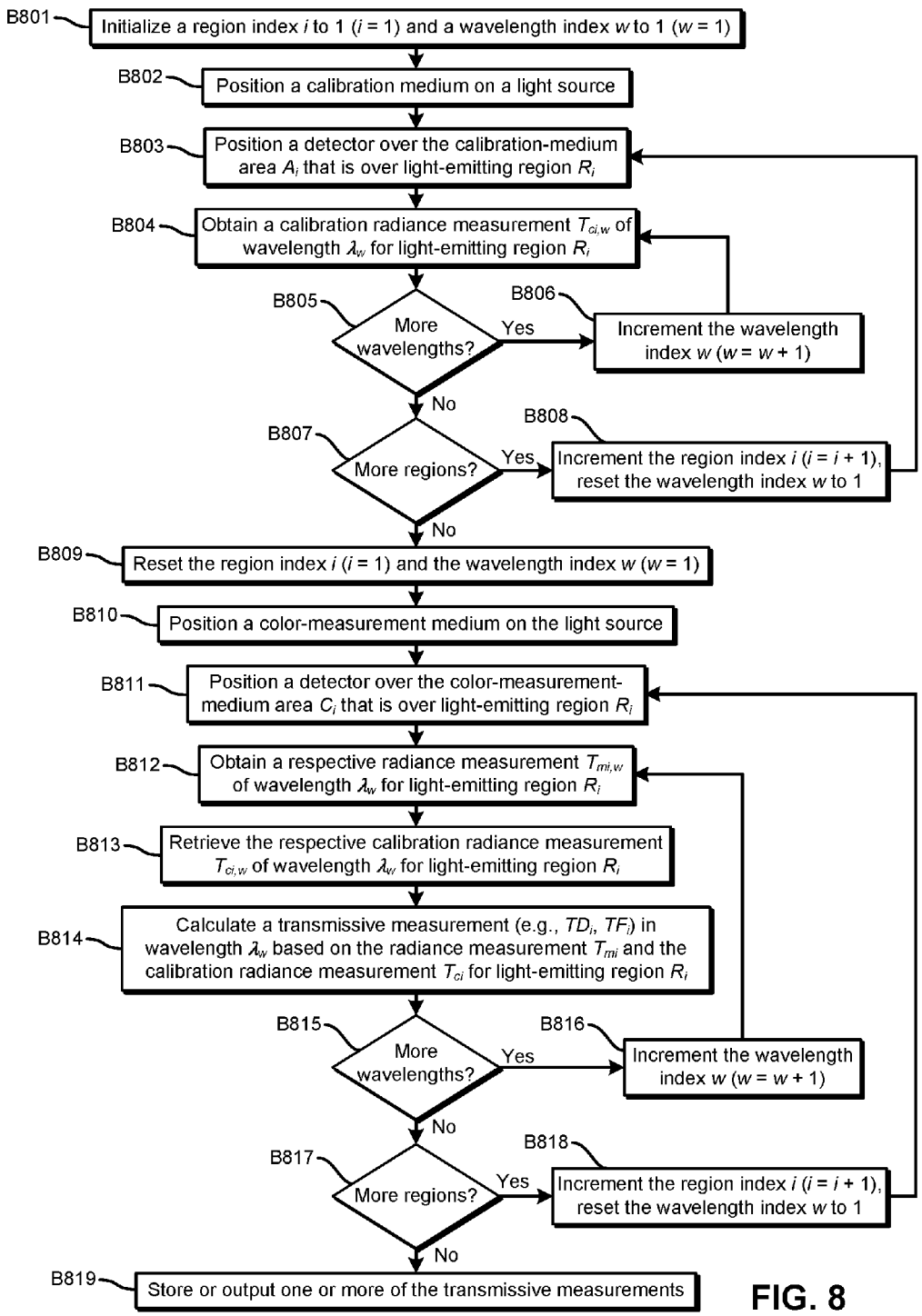
FIG. 8 illustrates an example embodiment of an operational flow for obtaining a spectral transmissive measurement of a medium.

FIG. 8 illustrates an example embodiment of an operational flow for obtaining a spectral transmissive measurement of a medium. This operational flow may be performed by a properly-configured embodiment of the system 100 in FIG. 2 or another specially-configured system (e.g., the system 1300 in FIG. 13).

The flow begins in block B801, where the system initializes a region index i to one and initializes a wavelength index w to one. Next, in block B802, the system positions a calibration medium on a light source, which includes light-emitting regions, or the system prompts a user to position the calibration medium on the light source. The flow then moves to block B803, where the system positions the detector over the calibration-medium area $A_i$ that is over light-emitting region $R_i$ or prompts the user to position the detector over the calibration-medium area $A_i$ that is over light-emitting region $R_i$. Next, the system obtains and stores a respective calibration radiance measurement $T_{c_{i,w}}$ of light at wavelength $\lambda_w$ for light-emitting region $R_i$.

Next, in block B805, the system determines if a calibration radiance measurement $T_{c_{i,w}}$ of light in another wavelength $\lambda_w$ should be obtained for light-emitting region $R_i$. If yes (Yes in block B805), for example if a respective calibration radiance measurement $T_{c_{i,w}}$ has not been obtained for every wavelength in the wavelength range, then the flow moves to block B806, where the wavelength index w is increased by one. In some embodiments, block B806 increases the wavelength by one step size. For example, in some embodiments the wavelength step size for $\lambda_w$ is 2 nm, 5 nm, 10 nm, 15 nm, or 20 nm, and the wavelength range is 380 nm to 730 nm. After block B806, the flow returns to block B803. If not (No in block B805), then the flow proceeds to block B807.

In block B807, the system determines if a calibration radiance measurement is to be obtained for another region. If yes (Yes in block B807), then the flow moves to block B808, where the region index i is incremented and the wavelength index w is reset to one, and the flow returns to block B803. If not (No in block B807), then the flow proceeds to block B809.

In block B809, the system resets the region index i to one and resets the wavelength index w to one. Next, in block B810, the system positions a color-measurement medium on the light source. In some embodiments, the system prompts the user to position the color-measurement medium. The flow then moves to block B811, where the system positions a detector over the color-measurement-medium area $C_i$ that is over light-emitting region $R_i$. In some embodiments, the system prompts the user to position a detector over the color-measurement-medium area $C_i$ that is over the light-emitting region $R_i$. The flow then proceeds to block B812, where the system obtains a respective color radiance measurement $T_{m_{i,w}}$ of light at wavelength $\lambda_w$ for light-emitting region $R_i$.

Next, in block B813, the system retrieves the respective calibration radiance measurement $T_{c_{i,w}}$ of light at wavelength $\lambda_w$ for light-emitting region $R_i$, and in block B814 the system calculates a transmissive measurement (e.g., a transmittance-factor measurement $TF(\lambda)$, a transmissive-density measurement $TD(\lambda)$) of light at wavelength $\lambda_w$ for light-emitting region $R_i$ based on the color radiance measurement $T_{m_{i,w}}$ and the calibration radiance measurement $T_{c_{i,w}}$.

Next, in block B815, the system determines if another color radiance measurement $T_{m_{i,w}}$ of light at another wavelength $\lambda_w$ should be obtained for light-emitting region $R_i$. If yes (Yes in block B815), then the flow moves to block B816, where the wavelength index w is increased by one, and then the flow returns to block B812. If not (No in block B815), then the flow proceeds to block B817. In block B817, the system determines if a color radiance measurement is to be obtained for another region. If yes (Yes in block B817), then the flow moves to block B818, where the region index i is incremented and the wavelength index w is reset to one, and the flow returns to block B811. If not (No in block B817), then the flow proceeds to block B819. In block B819, the system stores or outputs one or more of the transmissive measurements.

Figure 9:
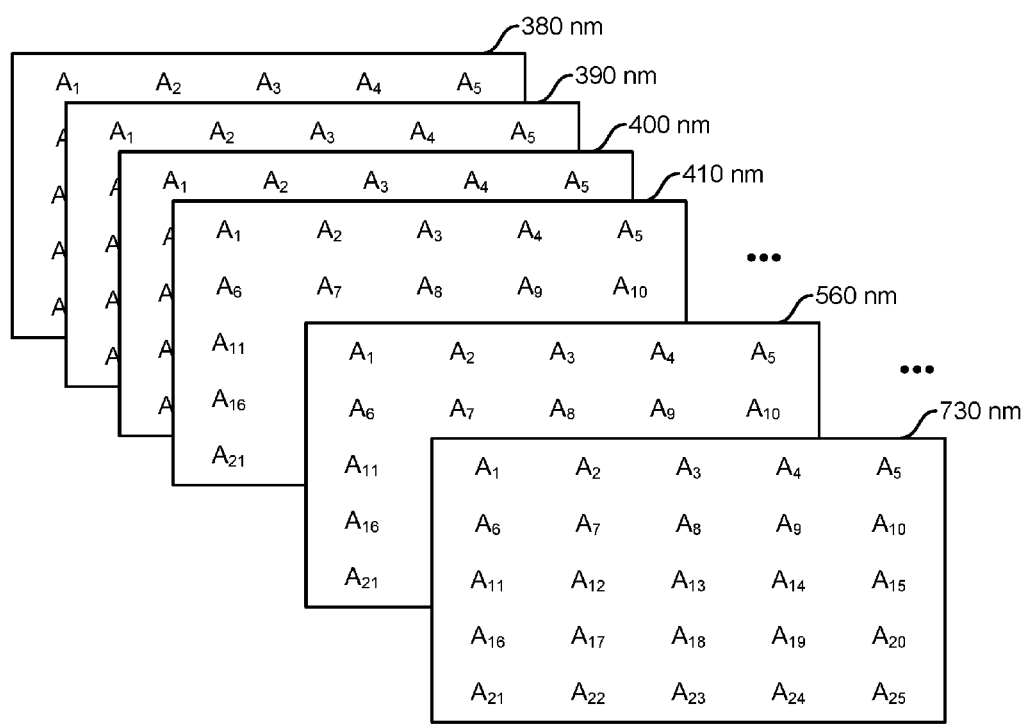
FIG. 9 is a conceptual illustration of an example embodiment of regions and their respective radiance measurements in different wavelengths.

FIG. 9 is a conceptual illustration of an example embodiment of regions and their respective radiance measurements in different wavelengths. In this embodiment, measurements of light at different wavelengths are taken for each region. The wavelength step size is 10 nm in this example embodiment, and the wavelength range goes from 380 nm to 730 nm. Thus, multiple radiance measurements are obtained for each region, each for a respective wavelength. For example, for region $A_2$, radiance measurements are obtained for 380 nm, 390 nm, 400 nm, 410 nm, . . . , 560 nm, . . . , and 730 nm. Other embodiments may have more or fewer regions, different wavelengths, larger or smaller wavelength step sizes, or different starting and ending wavelengths.

Figure 10A:
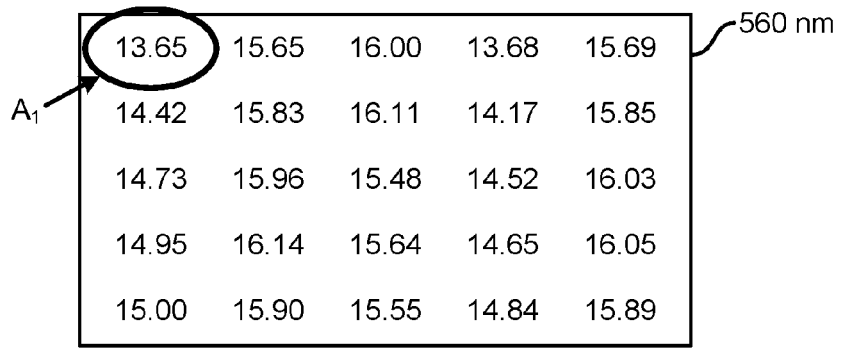
FIG. 10A illustrates example embodiments of calibration radiance measurements and the positions of the respective light-emitting regions where the calibration radiance measurements were obtained.
Figure 10B:
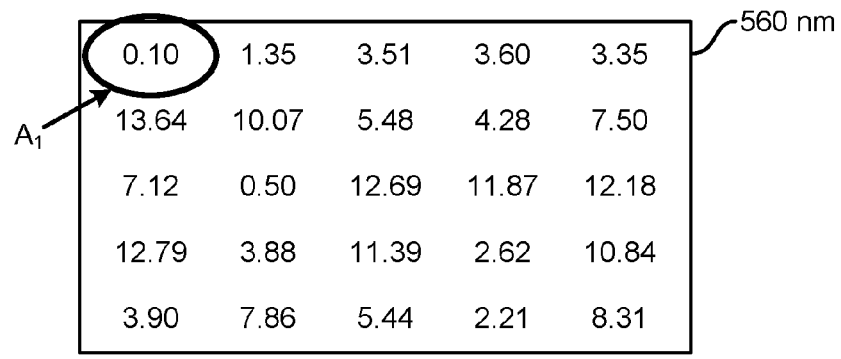
FIG. 10B illustrates example embodiments of color radiance measurements and the positions of the respective light-emitting regions where the color radiance measurements were obtained.

FIG. 10A illustrates example embodiments of calibration radiance measurements and the positions of the respective light-emitting regions where the calibration radiance measurements were obtained. These calibration radiance measurements were taken at a wavelength of 560 nm. For example, for region $A_1$, the calibration radiance measurement at 560 nm is 13.65. FIG. 10B illustrates example embodiments of color radiance measurements and the positions of the respective light-emitting regions where the color radiance measurements were obtained. These color radiance measurements were also taken at a wavelength of 560 nm. For example, for region $A_1$, the color radiance measurement at 560 nm is 0.10.

Figure 10C:
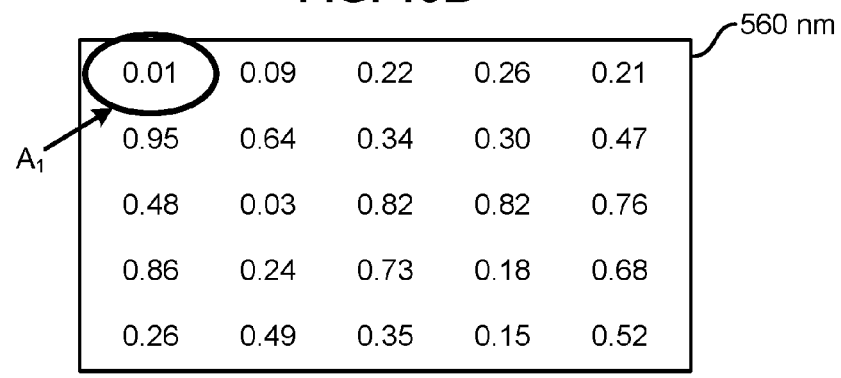
FIG. 10C illustrates example embodiments of transmittance-factor measurements that were generated based on the calibration radiance measurements in FIG. 10A and on the color radiance measurements in FIG. 10B.

FIG. 10C illustrates example embodiments of transmittance-factor measurements that were generated based on the calibration radiance measurements in FIG. 10A and on the color radiance measurements in FIG. 10B. For example, the transmittance-factor measurement for region $A_1$ is based on the calibration radiance measurement at region $A_1$ in FIG. 10A and on the color radiance measurement at region $A_1$ in FIG. 10B. These transmittance-factor measurements indicate the transmittance factor of the medium at a wavelength of 560 nm.

Figure 10D:
FIG. 10D illustrates example embodiments of transmissive-density measurements that were generated based on the calibration radiance measurements in FIG. 10A and on the color radiance measurements in FIG. 10B.

FIG. 10D illustrates example embodiments of transmissive-density measurements that were generated based on the calibration radiance measurements in FIG. 10A and on the color radiance measurements in FIG. 10B. For example, the transmissive-density measurement for region $A_1$ is based on the calibration radiance measurement at region $A_1$ in FIG. 10A and on the color radiance measurement at region $A_1$ in FIG. 10B. These transmissive-density measurements indicate the transmissive density of the medium at a wavelength of 560 nm.

In the embodiments shown of FIGS. 10A-D, the measurements are stored in a map form, which identifies the respective locations of the regions where the measurements were taken. Other embodiments may store the measurements in other forms, including other forms that store measurements and the respective locations where the measurements were taken.

Figure 11A:
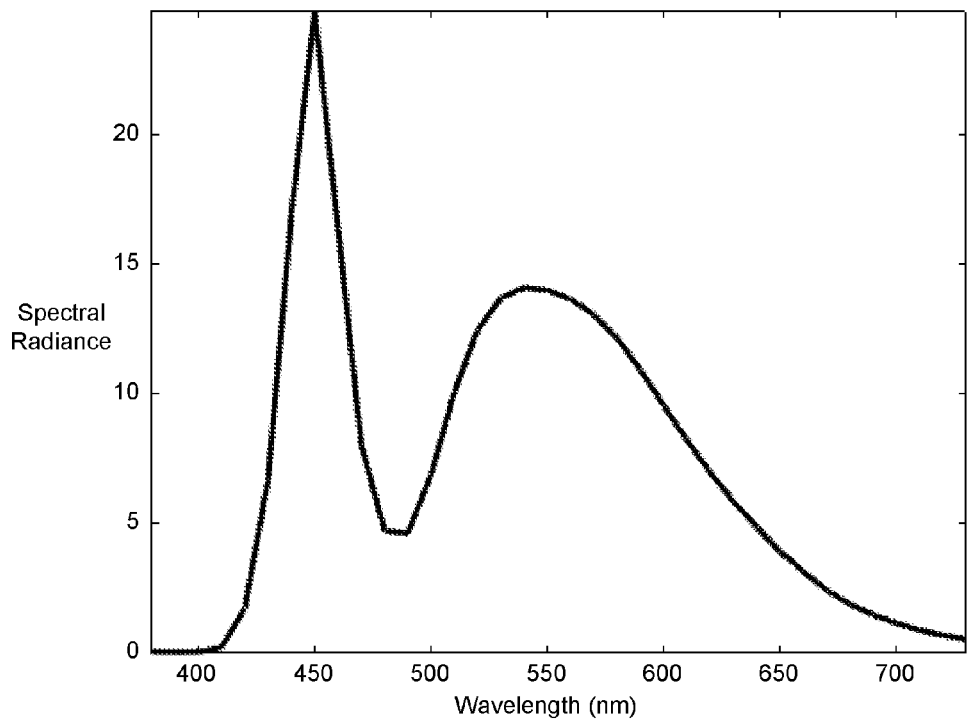
FIG. 11A is a graph that illustrates an example embodiment of the spectral radiance at different wavelengths for light, from a light-emitting region, that passed through a calibration medium and that was detected by a detector.
Figure 11B:
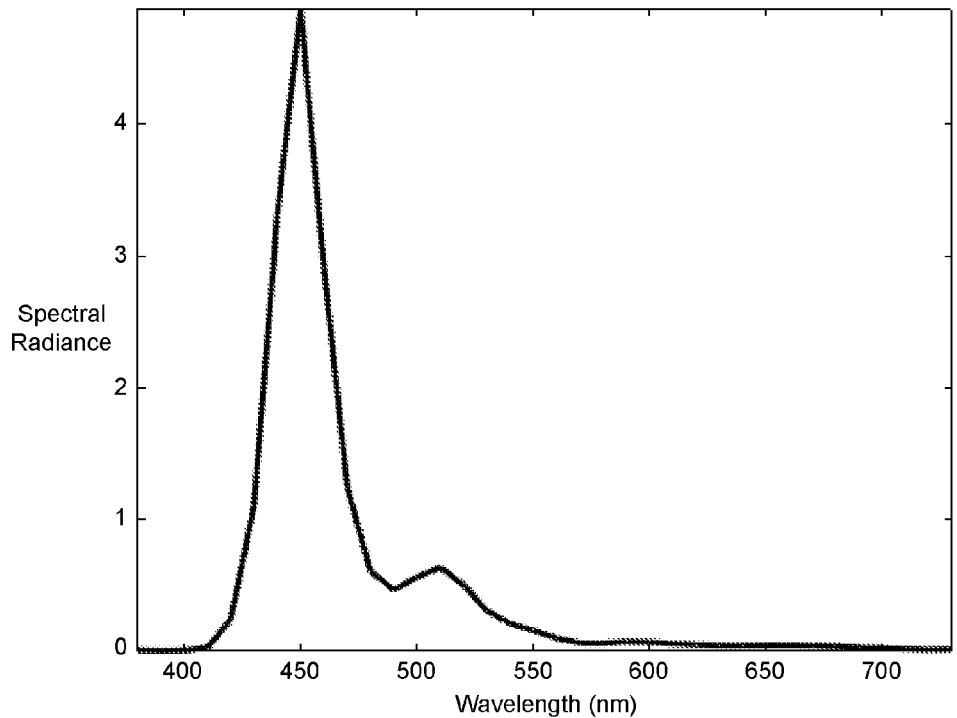
FIG. 11B is a graph that illustrates an example embodiment of the spectral radiance at different wavelengths for light, from a light-emitting region, that passed through a color patch on a medium and that was detected by a detector.

FIG. 11A is a graph that illustrates an example embodiment of the spectral radiance at different wavelengths for light from light-emitting region $A_1$ in FIG. 10A that passes through a calibration medium. As shown in FIG. 11A, the spectral radiance of a light-emitting region in different wavelengths may not be the same. Also, FIG. 11B is a graph that illustrates an example embodiment of the spectral radiance at different wavelengths for light from light-emitting region $A_1$ in FIG. 10B that passes through a color patch on a color-measurement medium. As shown in FIG. 11B, the spectral radiance in different wavelengths may not be the same.

Figure 12A:
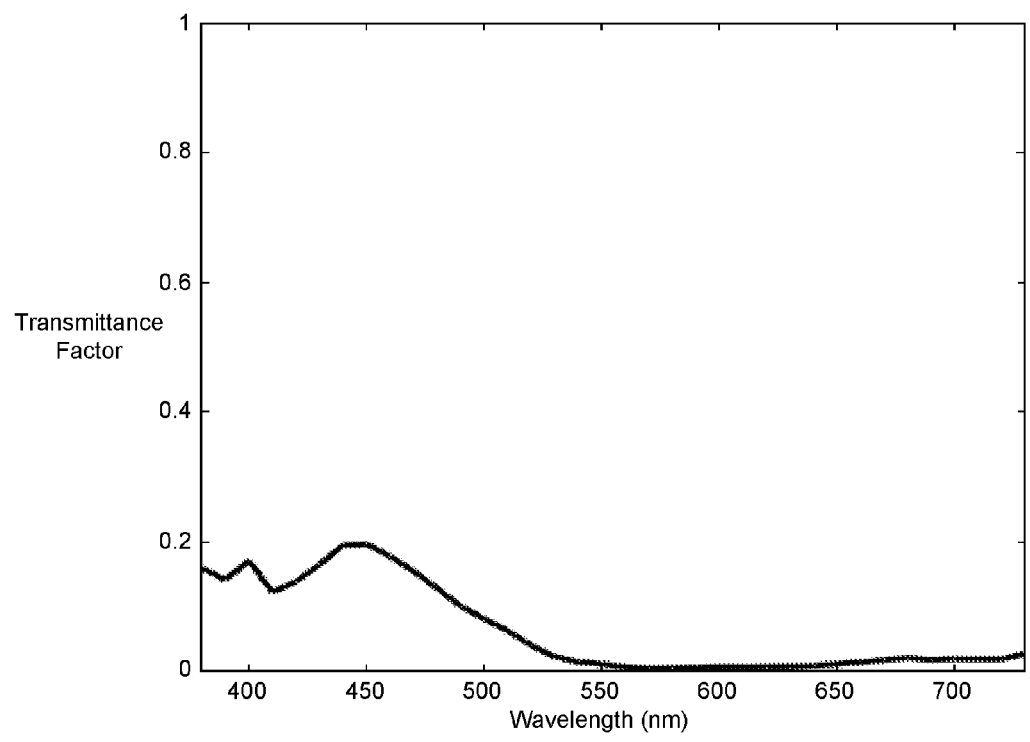
FIG. 12A is a graph that illustrates an example embodiment of the transmittance factor at different wavelengths for light from a light-emitting region.

FIG. 12A is a graph that illustrates an example embodiment of the transmittance factor at different wavelengths for light from light-emitting region $A_1$. The transmittance-factor measurements were generated based on the radiance measurements in FIG. 11A, on the radiance measurements in FIG. 11B, and on equation (1).

Figure 12B:
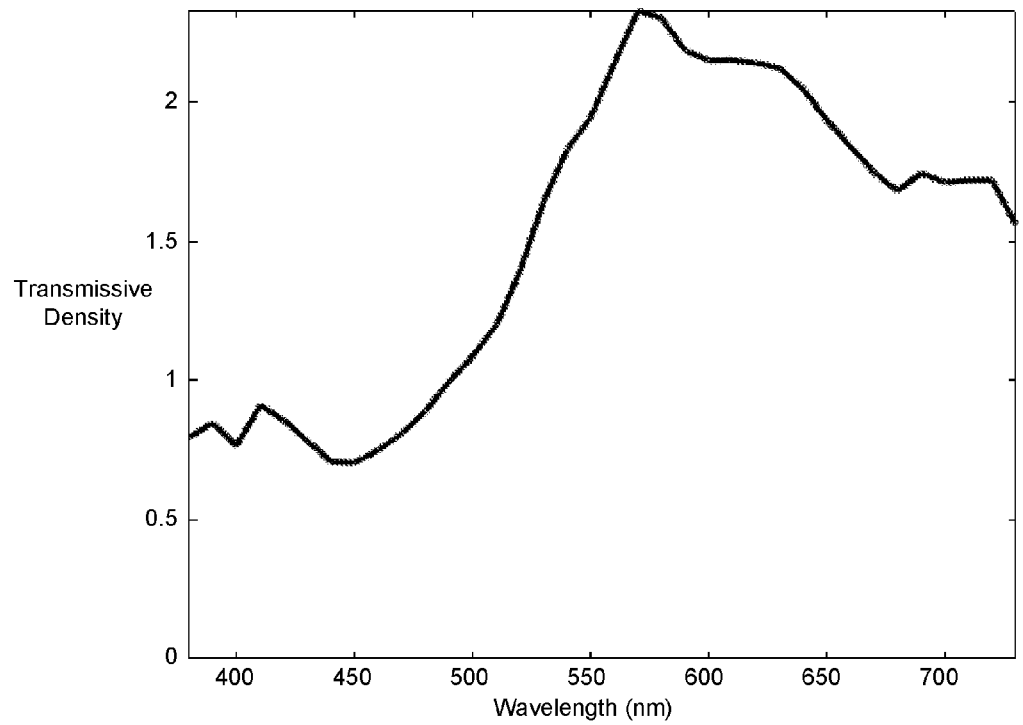
FIG. 12B is a graph that illustrates an example embodiment of the transmissive density at different wavelengths for light from a light-emitting region.

FIG. 12B is a graph that illustrates an example embodiment of the transmissive density at different wavelengths for light from light-emitting region $A_1$. The transmissive-density measurements were generated based on the radiance measurements in FIG. 11A, on the radiance measurements in FIG. 11B, and on equation (2).

Figure 13:
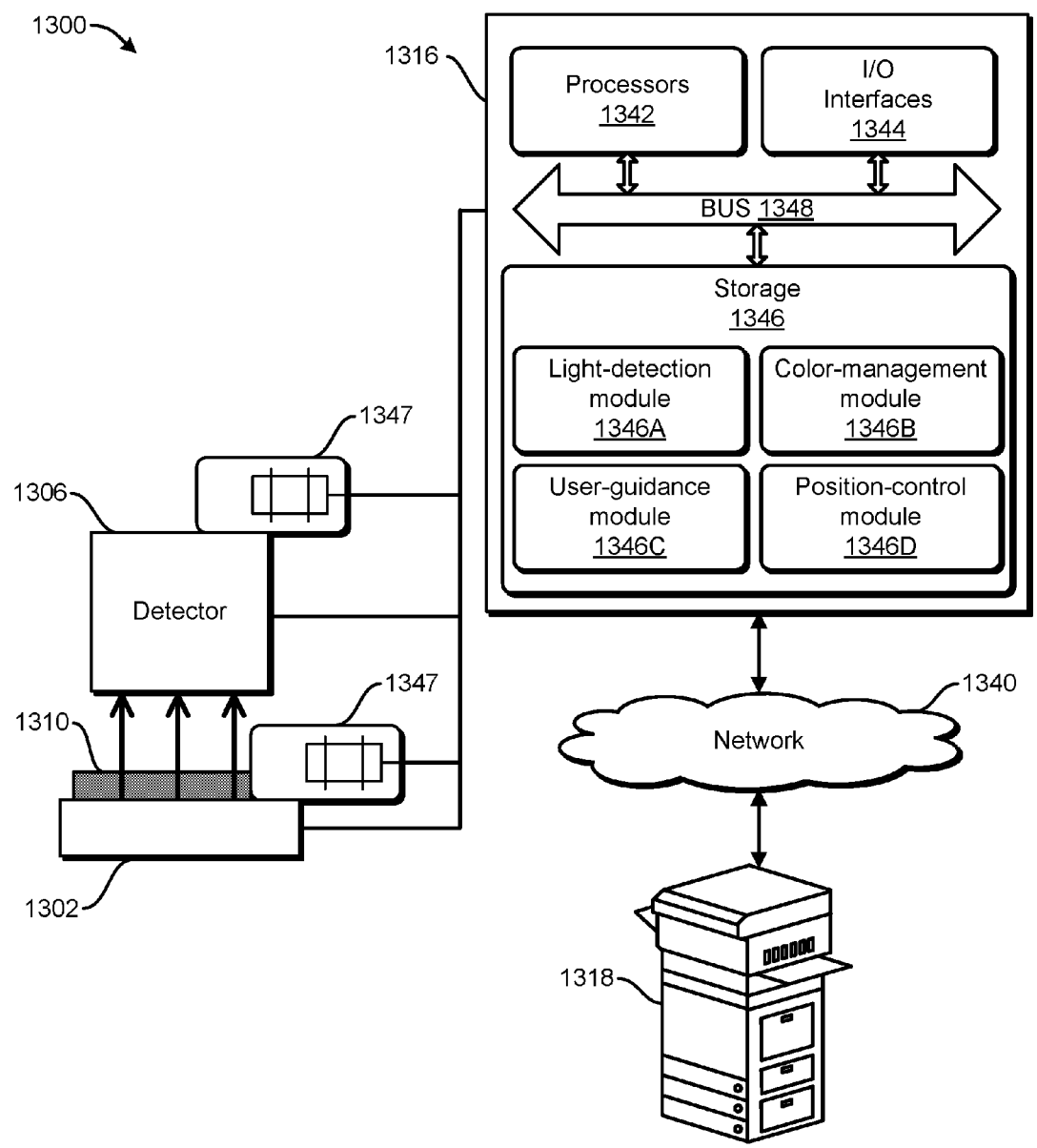
FIG. 13 illustrates an example embodiment of a system for obtaining a spectral transmissive measurement of a medium.

FIG. 13 illustrates an example embodiment of a system 1300 for obtaining spectral transmissive measurements for media (e.g., media for a backlit display). The system 1300 includes a detector 1306, a computing device 1316, a light source 1302, and a printing apparatus 1318. This example embodiment of a system 1300 also includes two movement mechanisms 1347, one of which is configured to move the detector 1306, and the other of which is configured to move a medium 1310. In this example embodiment, the computing device 1316 and the printing apparatus 1318 are capable of communicating by means of one or more networks 1340, which may include a LAN, a WAN, a MAN, and PAN. In some embodiments, the computing device 1316 and the printing apparatus 1318 communicate by means of another wired or wireless channel, and similarly the other components of the system 1300 may also be capable of communicating with each other by means of the same network 1340, a different network, or other wired or wireless channels.

The computing device 1316 includes one or more processors 1342, one or more I/O interfaces 1344, and storage 1346. Also, the hardware components of the computing device 1316 communicate by means of one or more buses 1348 or other electrical connections. Examples of buses include a universal serial bus (USB), an IEEE 1394 bus, a PCI bus, an Accelerated Graphics Port (AGP) bus, a Serial AT Attachment (SATA) bus, and a Small Computer System Interface (SCSI) bus.

The one or more processors 1342 include one or more central processing units (CPUs), which include microprocessors (e.g., a single core microprocessor, a multi-core microprocessor); graphics processing units (GPUs); or other electronic circuitry. The one or more processors 1342 are configured to read and perform computer-executable instructions, such as instructions that are stored in the storage 1346. The I/O interfaces 1344 include communication interfaces for input and output devices, which may include a keyboard, a display device, a mouse, a printing device, a touch screen, a light pen, an optical-storage device, a scanner, a microphone, a drive, a controller (e.g., a joystick, a control pad), and a network interface controller.

The storage 1346 includes one or more computer-readable storage media. As used herein, a computer-readable storage medium, in contrast to a mere transitory, propagating signal per se, refers to a computer-readable media that includes a tangible article of manufacture, for example a magnetic disk (e.g., a floppy disk, a hard disk), an optical disc (e.g., a CD, a DVD, a Blu-ray), a magneto-optical disk, magnetic tape, and semiconductor memory (e.g., a non-volatile memory card, flash memory, a solid-state drive, SRAM, DRAM, EPROM, EEPROM). Also, as used herein, a transitory computer-readable medium refers to a mere transitory, propagating signal per se, and a non-transitory computer-readable medium refers to any computer-readable medium that is not merely a transitory, propagating signal per se. The storage 1346, which may include both ROM and RAM, can store computer-readable data or computer-executable instructions.

While the components of the computing device 1316 may contained in a single housing, such as a personal computer or server, in some embodiments the components of the computing device 1316 are distributed across a plurality of different housings or locations. For example, the computing device 1316 may contain one or more remotely-distributed processors 1342 and storage 1346 that can be accessed for processing and storage of data and information, such as in a cloud computing system.

The computing device 1316 also includes a light-detection module 1346A, a color-management module 1346B, a user-guidance module 1346C, and a position-control module 1346D. A module includes logic, computer-readable data, or computer-executable instructions, and may be implemented in software (e.g., Assembly, C, C++, C#, Java, BASIC, Perl, Visual Basic), hardware (e.g., customized circuitry), or a combination of software and hardware. In some embodiments, the computing device 1316 includes additional or fewer modules, the modules are combined into fewer modules, or the modules are divided into more modules. When the modules are implemented in software, the software can be stored in the storage 1346.

The light-detection module 1346A includes instructions that, when executed, or circuits that when activated, cause the computing device 1316 to communicate with the detector 1306 to obtain information related to the detection of light emitted from the light source 1302, such as the calibration-measurement information (e.g., a spectral-radiance measurement from a calibration medium) and color-measurement information (e.g., a spectral-radiance measurement from a color-measurement medium). The light-detection module 1346A can cause the computing device 1316 to receive the information from the detector 1306, and may also perform processing on the received information, such as signal processing. The light-detection module 1346A can cause the information received from the detector 1306 to be stored in the storage 1346. In some embodiments, the light-detection module 1346 causes the detector 1306 to initiate the light detection, for example when a proper alignment of a medium 1310 with respect to one or both of the light source 1302 and the detector 1306 is recognized. In some embodiments of the light-detection module 1346A, these operations include one or more of the operations in blocks B2 and B5 of FIG. 3; blocks B13-B14 and B17-B18 of FIG. 5; blocks B23, B24, B29, and B32 in FIG. 6; blocks B73, B74, B77, and B78 in FIG. 7; and blocks B804, B805, B807, B812, B815, and B817 in FIG. 8. The light-detection module 1346A may also be capable of causing the computing device 1316 to communicate with the light source 1302, for example to perform the operations of blocks B1 and B4 of FIG. 3.

The color-management module 1346B includes instructions that, when executed, or circuits that when activated, cause the computing device 1316 to perform color management, such as color-information determination based on the radiance measurements, as well as to communicate with the printing apparatus 1318 to print images according to the determined color information. In some embodiments of the color-management module 1346B, these operations include one or more of the operations in block B6 in FIG. 3; block B19 in FIG. 5; blocks B30, B31, and B34 in FIG. 6; and block B79 in FIG. 7.

The user-guidance module 1346C includes instructions that, when executed, or circuits that when activated, cause the computing device 1316 to provide guidance to a user to perform a process for obtaining measurements of a medium, such as by prompting the user to position one or more of the medium 1310 and the detector 1306 with respect to alignment markings to obtain the radiance measurements. In some embodiments of the user-guidance module 1346C, these operations include one or more of the operations in blocks B11-B12 and B15-B16 in FIG. 5 and in blocks B21-B22 and B27-B28 in FIG. 6.

The position-control module 1346D includes instructions that, when executed, or circuits that when activated, cause the computing device 1316 to control one or more of the movement mechanisms 1347 to position the medium 1310 or the detector 1306 relative to the light source 1302. In some embodiments of the position-control module 1346D, these operations include one or more of the operations in blocks B71, B72, B74, and B76 in FIG. 7 and in blocks B802, B803, B810, and B811 in FIG. 8.

The above-described devices, systems, and methods can be implemented, at least in part, by providing one or more computer-readable media that contain computer-executable instructions for realizing the above-described operations to one or more computing devices that are configured to read and execute the computer-executable instructions. The systems, apparatuses or devices perform the operations of the above-described embodiments when executing the computer-executable instructions. Also, an operating system on the one or more systems, apparatuses or devices may implement at least some of the operations of the above-described embodiments.

Any applicable computer-readable medium (e.g., a magnetic disk (including a floppy disk, a hard disk), an optical disc (including a CD, a DVD, a Blu-ray disc), a magneto-optical disk, a magnetic tape, and semiconductor memory (including flash memory, DRAM, SRAM, a solid state drive, EPROM, EEPROM)) can be employed as a computer-readable medium for the computer-executable instructions. The computer-executable instructions may be stored on a computer-readable storage medium that is provided on a function-extension board inserted into a device or on a function-extension unit connected to the device, and a CPU provided on the function-extension board or unit may implement at least some of the operations of the above-described embodiments.

Furthermore, some embodiments use one or more functional units to implement the above-described devices, systems, and methods. The functional units may be implemented in only hardware (e.g., customized circuitry) or in a combination of software and hardware (e.g., a microprocessor that executes software).

The scope of the claims is not limited to the above-described embodiments and includes various modifications and equivalent arrangements. Also, as used herein, the conjunction "or" generally refers to an inclusive "or," though "or" may refer to an exclusive "or" if expressly indicated or if the context indicates that the "or" must be an exclusive "or."

What is claimed is:

1. A method of obtaining color information for printing on media, the method comprising:

illuminating one or more areas on a calibration medium from a first side of the calibration medium with one or more respective light-emitting regions of a diffused light source;

detecting, at a second side of the calibration medium that is opposite to the first side, light transmitted through the calibration medium at the one or more areas, thereby obtaining calibration-measurement information for at least one of the one or more light-emitting regions;

illuminating one or more color patches on a color-measurement medium from a first side of the color-measurement medium with the one or more respective light-emitting regions of the light source;

detecting, at a second side of the color-measurement medium that is opposite to the first side, light transmitted through the one or more color patches printed on the color-measurement medium, thereby obtaining color-measurement information for at least one of the one or more light-emitting regions; and determining one or more transmissive measurements based on the calibration-measurement information and the color-measurement information.

2. The method of claim 1, wherein the calibration medium and the color-measurement medium are the same medium.

3. The method of claim 1, wherein the calibration medium and the color-measurement medium are different instances of one type of medium.

4. The method of claim 1, further comprising determining color-calibration information for a printing apparatus based on the one or more transmissive measurements.

5. The method of claim 1, wherein detecting, at the second side of the calibration medium that is opposite to the first side, light transmitted through the calibration medium at the one or more areas, thereby obtaining calibration-measurement information for at least one of the one or more light-emitting regions includes detecting light transmitted through a plurality of areas on the calibration medium, thereby obtaining calibration-measurement information for two or more of the light-emitting regions.

6. The method of claim 1, wherein the one or more transmissive measurements are transmissive-density measurements that can be described by the following:

$$TD(\lambda) = -\log_{10}\left(\frac{T_m(\lambda)}{T_c(\lambda)}\right),$$

where $T_m(\lambda)$ is a spectral radiance measurement for light at a wavelength $\lambda$ that is included in the color-measurement information, where $T_c(\lambda)$ is a spectral radiance measurement for light at the wavelength $\lambda$ that is included in the calibration-measurement information, and where $TD(\lambda)$ is a transmissive-dentity measurement for light at the wavelength $\lambda$.

7. The method of claim 1, wherein the one or more transmissive measurements are transmittance-factor measurements that can be described by the following:

$$TF(\lambda) = \frac{T_m(\lambda)}{T_c(\lambda)},$$

where $T_m(\lambda)$ is a spectral radiance measurement for light at a wavelength $\lambda$ that is included in the color-measurement information, where $T_c(\lambda)$ is a spectral radiance measurement for light at the wavelength $\lambda$ that is included in the calibration-measurement information, and where $TF(\lambda)$ is a transmittance-factor measurement for light at the wavelength $\lambda$.

8. A system comprising:

one or more computer-readable media; and one or more processors that are coupled to the one or more computer-readable media and that are configured to cause the system to obtain a first calibration radiance measurement from a detector, wherein the first calibration radiance measurement is a measurement of light that is emitted by a first light-emitting region of a light source on a first side of a calibration medium, that is transmitted through the calibration medium at a first area, and that is measured by the detector on a second side of the calibration medium that is opposite to the first side;

obtain a first color radiance measurement from the detector, wherein the first color radiance measurement is a measurement of light that is emitted by the first light-emitting region of the light source on a first side of a color-measurement medium, that is transmitted through the color-measurement medium at a second area, and that is measured by the detector on a second side of the color-measurement medium that is opposite to the first side; and determine a respective transmissive measurement for the first light-emitting region based on the first calibration radiance measurement and on the first color radiance measurement.

9. The system of claim 8, wherein the one or more processors are further configured to cause the system to obtain a second calibration radiance measurement from the detector, wherein the second calibration radiance measurement is a measurement of light that is emitted by a second light-emitting region of the light source on the first side of the calibration medium, that is transmitted through the calibration medium at a third area, and that is measured by the detector on the second side of the calibration medium that is opposite to the first side, wherein the second-light emitting region is different from the first light-emitting region;

obtain a second color radiance measurement from the detector, wherein the second color radiance measurement is a measurement of light that is emitted by the second light-emitting region of the light source on the first side of the color-measurement medium, that is transmitted through the color-measurement medium at a fourth area, and that is measured by the detector on the second side of the color-measurement medium that is opposite to the first side; and determine a respective transmissive measurement for the second light-emitting region based on the second calibration radiance measurement and on the second color radiance measurement.

10. The system of claim 9, wherein the second area of the color-measurement medium and the fourth area of the color-measurement medium have respective color patches printed thereon, and the respective color patches have different colors.

11. The system of claim 8, wherein the one or more processors are further configured to cause the system to position the calibration medium, position the detector relative to the calibration medium, position the color-measurement medium, and position the detector relative to the color-measurement medium.

12. The system of claim 8, wherein the light source is a light panel, and the first light-emitting region and the second light-emitting region are each a respective region on a light-emitting surface of the light panel.

13. The system of claim 8, wherein the one or more processors are further configured to cause the system to
generate a prompt that identifies a predetermined position of the calibration medium; and
generate a prompt that identifies a predetermined position of the color-measurement medium.

14. The system of claim 13, wherein the one or more processors are further configured to cause the system to
generate a prompt that identifies the first area, wherein the first area is above the first light-emitting region; and
generate a prompt that identifies the second area, wherein the second area is above the second light-emitting region.

15. The system of claim 8, wherein the one or more processors are further configured to cause the system to
detect one or more alignment markings on the calibration medium;
generate a prompt in response to the detection of the one or more alignment markings on the calibration medium;
detect one or more alignment markings on the color-measurement medium; and
generate a prompt in response to the detection of the one or more alignment markings on the color-measurement medium.

16. One or more non-transitory computer-readable media that store computer-executable instructions that, when executed by one or more computing devices, cause the one or more computing devices to perform operations comprising:
obtaining one or more calibration radiance measurements from a detector, wherein each of the calibration radiance measurements is a measurement of light that is emitted by a respective light-emitting region of a light source on a first side of a calibration medium, that is transmitted through the calibration medium at a respective area of the calibration medium, and that is measured by the detector on a second side of the calibration medium that is opposite to the first side;
obtaining one or more color radiance measurements from the detector, wherein each of the color radiance measurements is a measurement of light that is emitted by a respective light-emitting region of the light source on a first side of a color-measurement medium, that is transmitted through the color-measurement medium at a respective area of the color-measurement medium, and that is measured by the detector on a second side of the color-measurement medium that is opposite to the first side; and
generating one or more transmissive measurements based on the one or more calibration radiance measurements and on the one or more color radiance measurements.

17. The one or more non-transitory computer-readable media of claim 16, wherein the operations further comprise:
generating color-calibration information for a printing apparatus based on the one or more transmissive measurements.

18. The one or more non-transitory computer-readable media of claim 16, wherein the operations further comprise:
causing a printing apparatus to print a plurality of color patches on the calibration medium, thereby creating the color-measurement medium.

19. The one or more non-transitory computer-readable media of claim 16, wherein the operations further comprise:
prompting a user to position the calibration medium at a respective predetermined position relative to the light source;
prompting the user to position the detector at a respective predetermined position relative to the calibration medium;
prompting the user to position the color-measurement medium at a respective predetermined position relative to the light source; and
prompting the user to position the detector at a respective predetermined position relative to the color-measurement medium.

20. The one or more non-transitory computer-readable media of claim 16, wherein the operations further comprise:
positioning the calibration medium,
positioning the detector relative to the calibration medium,
positioning the color-measurement medium, and
positioning the detector relative to the color-measurement medium.

* * * * *